US009561316B2

(12) United States Patent
Gerber et al.

(10) Patent No.: US 9,561,316 B2
(45) Date of Patent: Feb. 7, 2017

(54) INTERSESSION MONITORING FOR BLOOD FLUID REMOVAL THERAPY

(75) Inventors: Martin Gerber, Maple Grove, MN (US); Suping Lyu, Maple Grove, MN (US); Bryant Pudil, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 908 days.

(21) Appl. No.: 13/424,429

(22) Filed: Mar. 20, 2012

(65) Prior Publication Data

US 2012/0277551 A1 Nov. 1, 2012

Related U.S. Application Data

(60) Provisional application No. 61/480,539, filed on Apr. 29, 2011, provisional application No. 61/480,544, (Continued)

(51) Int. Cl.
*A61M 31/00* (2006.01)
*A61M 37/00* (2006.01)
(Continued)

(52) U.S. Cl.
CPC .......... *A61M 1/1603* (2014.02); *A61B 5/0031* (2013.01); *A61B 5/026* (2013.01);
(Continued)

(58) Field of Classification Search
CPC ....... A61B 5/00; A61B 5/0002; A61B 5/0006; A61B 5/02; A61B 5/021; A61B 5/022; A61B 5/024; A61B 5/0205; A61B 5/0215; A61B 5/02125; A61B 5/02225; A61B 5/0031; A61B 5/0428; A61B 5/0452; A61B 5/201; A61B 5/208; A61B 5/222; A61B 5/486; A61B 5/4839; A61B 5/14532;A61B 5/14539; A61B 5/14546; A61K 33/14; A61M 1/16; A61M 1/1601; A61M 1/1603; A61M 1/1605; A61M 1/1611; A61M 1/1613; A61M 1/1615; A61M 1/1647; A61M 1/1656; A61M 1/34; A61M 1/656; A61M 1/341; A61M 1/3403; A61M 1/3472; A61M 1/3609; A61M 1/3643; A61M 1/3679; A61M 5/142; A61M 5/1723; A61M 31/00; A61M 37/00; A61M 2001/165; A61M 2001/1609; A61M 2001/1666; A61M 2001/3437; B01D 11/00; B01D 21/30; B01D 61/00; B01D 61/08; B01D 61/12; B01D 67/0093; B01D 69/02; C02F 1/32; C02F 1/44; C02F 1/283; C02F 9/00; C02F 2209/005; C02F 2209/008
(Continued)

(56) References Cited

U.S. PATENT DOCUMENTS 5,092,886 A 3/1992 Dobos-Hardy
8,313,642 B2 11/2012 Yu et al.
(Continued)

FOREIGN PATENT DOCUMENTS

EP 1364666 A1 11/2003
WO 0066197 A1 11/2000
(Continued)

OTHER PUBLICATIONS

U.S. Appl. No. 61/480,539.
(Continued)

*Primary Examiner* — Dirk Bass
*Assistant Examiner* — Hayden Brewster
(74) *Attorney, Agent, or Firm* — Roger Hahn; Kenneth Collier

(57) ABSTRACT

Methods for monitoring patient parameters and blood fluid removal system parameters include identifying those system parameters that result in improved patient parameters or in worsened patent parameters. By comparing the patient's current parameters to past parameters in response to system parameters or changes in system parameters, a blood fluid removal system may be able to avoid future use of parameters that may harm the patient and may be able to learn which parameters are likely to be most effective in treating the patient in a blood fluid removal session.

13 Claims, 16 Drawing Sheets

Related U.S. Application Data filed on Apr. 29, 2011, provisional application No. 61/480,541, filed on Apr. 29, 2011, provisional application No. 61/480,535, filed on Apr. 29, 2011, provisional application No. 61/480,532, filed on Apr. 29, 2011, provisional application No. 61/480,530, filed on Apr. 29, 2011, provisional application No. 61/480,528, filed on Apr. 29, 2011.

(51) Int. Cl.
```
C02F 9/00      (2006.01)
B01D 61/00     (2006.01)
A61M 1/16      (2006.01)
A61B 5/145     (2006.01)
A61B 5/00      (2006.01)
A61B 5/026     (2006.01)
A61B 5/053     (2006.01)
A61M 1/34      (2006.01)
B01D 65/02     (2006.01)
A61M 1/00      (2006.01)
A61B 5/0295    (2006.01)
A61M 1/14      (2006.01)
B01D 61/32     (2006.01)
A61M 1/36      (2006.01)
A61M 1/28      (2006.01)
B01D 11/00     (2006.01)
```
(52) U.S. Cl.
CPC .......... *A61B 5/0295* (2013.01); *A61B 5/053* (2013.01); *A61B 5/0537* (2013.01); *A61B 5/145* (2013.01); *A61B 5/14503* (2013.01); *A61B 5/14535* (2013.01); *A61B 5/14539* (2013.01); *A61B 5/14546* (2013.01); *A61B 5/4836* (2013.01); *A61B 5/4848* (2013.01); *A61B 5/4875* (2013.01); *A61B 5/6866* (2013.01); *A61B 5/7282* (2013.01); *A61M 1/00* (2013.01); *A61M 1/14* (2013.01); *A61M 1/16* (2013.01); *A61M 1/1601* (2014.02); *A61M 1/1605* (2014.02); *A61M 1/1607* (2014.02); *A61M 1/1613* (2014.02); *A61M 1/28* (2013.01); *A61M 1/34* (2013.01); *A61M 1/342* (2013.01); *A61M 1/3607* (2014.02); *A61M 1/3609* (2014.02); *A61M 1/3672* (2013.01); *B01D 61/00* (2013.01); *B01D 61/32* (2013.01); *B01D 65/02* (2013.01); *A61B 2560/0223* (2013.01); *A61M 2202/0498* (2013.01); *A61M 2205/04* (2013.01); *A61M 2205/18* (2013.01); *A61M 2205/33* (2013.01); *A61M 2205/3303* (2013.01); *A61M 2205/3334* (2013.01); *A61M 2205/3523* (2013.01); *A61M 2205/50* (2013.01); *A61M 2205/52* (2013.01); *A61M 2205/60* (2013.01); *A61M 2205/70* (2013.01); *A61M 2230/00* (2013.01); *A61M 2230/005* (2013.01); *A61M 2230/20* (2013.01); *A61M 2230/207* (2013.01); *A61M 2230/208* (2013.01); *A61M 2230/65* (2013.01); *B01D 2321/12* (2013.01); *B01D 2321/40* (2013.01)

(58) Field of Classification Search
USPC .............. 210/647, 96.2, 143, 645, 646, 739; 600/300, 309, 483, 485, 508
See application file for complete search history.

(56) References Cited

U.S. PATENT DOCUMENTS

| | | |
|---|---|---|
| 2002/0042561 A1 | 4/2002 | Schulman et al. |
| 2006/0025661 A1 | 2/2006 | Sweeney et al. |
| 2006/0226079 A1 | 10/2006 | Mori et al. |
| 2007/0175827 A1* | 8/2007 | Wariar ............... A61M 1/1613 210/645 |
| 2007/0215545 A1 | 9/2007 | Bissler |
| 2008/0067132 A1 | 3/2008 | Ross et al. |
| 2008/0215247 A1 | 9/2008 | Tonelli et al. |
| 2009/0101577 A1 | 4/2009 | Fulkerson et al. |
| 2009/0275883 A1 | 11/2009 | Chapman et al. |
| 2010/0094158 A1 | 4/2010 | Solem et al. |
| 2013/0274644 A1* | 10/2013 | Hertz .................... A61M 1/16 604/6.09 |

FOREIGN PATENT DOCUMENTS

| | | | | |
|---|---|---|---|---|
| WO | | 0185295 A2 | 11/2001 | |
| WO | WO 2010028860 A1 * | | 3/2010 | ............ A61M 1/16 |

OTHER PUBLICATIONS

U.S. Appl. No. 61/480,544.
U.S. Appl. No. 61/480,541.
U.S. Appl. No. 61/480,535.
U.S. Appl. No. 61/480,532.
U.S. Appl. No. 61/480,530.
U.S. Appl. No. 61/480,528.
Roberts M, The regenerative dialysis (REDY) sorbent system. Nephrology, 1998, 275-278 :4.
Brynda, et. al., The detection of human β2-microglobulin by grating coupler immunosensor with three dimensional antibody networks, Biosensors & Bioelectronics. 1999, 363-368, 14(4).
Nedelkov, et. al., Design of buffer exchange surfaces and sensor chips for biosensor chip mass spectrometry, Proteomics, 2002, 441-446, 2(4).
Hemametrics, Crit-Line Hematocrit Accuracy, 2003, 1-5. vol. 1. Tech Note No. 11 (Rev. D).
Siegenthalar, et. al., Pulmonary fluid status monitoring with intrathoracic impedance, Journal of Clinical Monitoring and Computing, 2010, 449-451 : 24.
Wang, Fundamentals of intrathoracic impedance monitoring in heart failure, Am. J. Cardiology, 2007, 3G-310 : Suppl.
Bleyer, et. al., Sudden and cardiac death rates in hemodialysis patients. Kidney International, 1999, 1553-1559 : 55.
Zhong, et. al., Miniature urea sensor based on H(+)-ion sensitive field effect transistor and its application in clinical analysis, Chin. J. Biotechnol., 1992, 57-65, 8(1).
PCT/US2012/034331 International Search Report. Jul. 9, 2012.
PST/US2012/034334 International Search Report, Jul. 6, 2012.
PCT/US2012/034335 International Search Report, Sep. 5, 2012—(Copy attached herewith.).
PCT/US2013/034327 International Search Report, Aug. 13, 2013—(Copy attached herewith.).
PCT/US2012/034329 International Search Report Dec. 3, 2012—(Copy attached herewith.).
Roberts M, The regenerative dialysis (REDY) sorbent system, Nephrology, 1998, 275-278 : 4.
Brynda, et. al., The detection of human β2-microglobulin by grating coupler immunosensor with three dimensional antibody networks, Biosensors & Bioelectronics, 1999, 363-368, 14(4).

(56) References Cited

OTHER PUBLICATIONS

Hemarnetrics, Crit-Line Hematocrit Accuracy, 2003, 1-5, vol. 1, Tech Note No. 11 (Rev. D).
Wang, Fundamentals of intrathoracic impedance monitoring heart failure, Am. J. Cardiology, 2007, 3G-310: Suppl.
Bleyer, et. al., Sudden and cardiac death rates in hemodialysis patients, Kidney International, 1999, 1553-1559 : 55.
Zhong, et, al., Miniature urea sensor based on H(+)-ion sensitive field effect transistor and its application in clinical analysis, Chin. J. Biotechnol., 1992, 57-65, 8(1).
PCT/US2012/034334 International Search Report, Jul. 6, 2012.
PCT/US2012/034331 International Search Report, Jul. 9, 2012.

\* cited by examiner

INTERSESSION MONITORING FOR BLOOD FLUID REMOVAL THERAPY

RELATED APPLICATION

This application claims priority to U.S. Provisional Application No. 61/480,539, U.S. Provisional Application No. 61/480,544, U.S. Provisional Application No. 61/480,541, U.S. Provisional Application No. 61/480,535, U.S. Provisional Application No. 61/480,532, U.S. Provisional Application No. 61/480,530, and U.S. Provisional Application No. 61/480,528, wherein each priority application was filed Apr. 29, 2011, wherein each priority application is hereby incorporated by reference in its entirety to the extent that it does not conflict with the disclosure presented herein.

FIELD

The present disclosure relates generally to devices, systems and methods for monitoring parameters of patients that receive blood fluid removal therapy.

BACKGROUND

Patients who undergo hemodialysis or other procedures that remove fluid from blood often die of cardiac complications. Many factors may contribute to such death, including stress placed on the heart due to increased blood fluid volume in these patients. Increased fluid concentrations and inability to appropriately remove waste products from the blood can also contribute to electrolyte and pH imbalance that can affect cardiac contractility and efficiency. Further, rapid changes in fluid volume or pH or electrolyte concentration of the blood during hemodialysis or other fluid removal processes may place additional stress on the heart and may contribute to the high rate of morbidity for patients who undergo blood fluid removal procedures.

When a patient reaches a point where routine blood fluid removal procedures are prescribed, the patient undergoes periodic examinations that allow a healthcare provider to set various parameters of the blood fluid removal procedures, such as the profile of fluid removal, the composition of dialysate or replacement fluid employed, and the like. These examinations typically occur once a month in accordance with current standards of care.

While such monthly examinations somewhat provide for blood fluid removal sessions tailored according to the patient's needs, it may be desirable to provide a more systematic evaluation of the patient and the blood fluid removal session parameters to achieve a more patient-specific therapy.

SUMMARY

This disclosure, among other things, describes devices, systems and methods for monitoring patient parameters and blood fluid removal system parameters and identifying those system parameters that result in improved (more effective) patient parameters or in worsened (less effective) patent parameters. By comparing the patient's past responses to system parameters or changes in system parameters, a blood fluid removal system may be able to avoid future use of parameters that may harm the patient and may be able to learn which parameters are likely to be most effective in treating the patient in a blood fluid removal session. Further, by monitoring the patient's response between sessions, those system parameters that result in lasting improvement or worsening of patient variables may be tracked so that future blood fluid removal sessions may be appropriately tailored to effectuate good lasting outcomes for the patient. In addition or alternatively, tracking patient variables leading up to a blood fluid session may allow proper conditions to be set for the upcoming session based on patient response to prior system parameters when the patient presented with similar variables.

In various embodiments described herein, a method includes (i) storing system parameters from a first blood fluid removal session in memory; (ii) acquiring a first set of data regarding one or more patient parameters following the first session but before a second session; (iii) storing the first data set in a "most effective to date" data set memory; (iv) associating the first system parameters in an increased effectiveness lookup table with the first data set; (v) storing system parameters from the second blood fluid removal session in memory; (vi) acquiring a second set of data regarding the one or more patient parameters following the second session; and (vii) if at least one value of the second data set is closer to the target value than a corresponding at least one value of the first data set: replacing the first data set in the most effective to date data set memory with the second data set; storing in the increased effectiveness lookup table data regarding the second data set; and associating data regarding the second system parameters with the second data set.

In embodiments, a method includes (i) acquiring data regarding one or more of one or more patient physiological parameters and time since last blood fluid removal session; (ii) acquiring data regarding one or more target outcomes of a blood fluid removal session; (iii) comparing the data regarding at least one of the one or more target outcomes of the blood fluid removal session to corresponding data regarding at least one prior target outcome stored in a lookup table, wherein the lookup table comprises data regarding system parameters used in one or more prior blood fluid removal sessions of the patient and comprises patient data prior to the previous session regarding one or more of the one or more patient physiological parameters and the time since last blood fluid removal session; (iv) comparing the data regarding the one or more of the one or more patient physiological parameters and the time since last blood fluid removal session to corresponding patient data prior to the previous session stored in the lookup table; and (v) initiating a blood fluid removal session employing the system parameters used for the prior blood fluid removal session if the at least one of the one or more target outcomes is within a predetermined range of the corresponding data regarding the at least one prior target outcome stored in the lookup table and the data regarding the one or more of the one or more patient physiological parameters and the time since last blood fluid removal session is within a predetermined range of the corresponding patient data prior to the previous session stored in the lookup table.

Blood fluid removal systems configured to carry out the methods described herein are also presented, as are computer-readable medium that, when executed, cause a blood fluid removal system to carry out the methods described herein.

One or more embodiments of the systems, devices and methods described herein may provide one or more advantages over prior systems, devices and methods for blood fluid removal in patients. Such advantages will be apparent to those skilled in the art upon reading the following detailed description.

BRIEF DESCRIPTION OF THE DRAWINGS

The accompanying drawings, which are incorporated into and form a part of the specification, illustrate several embodiments of the present disclosure and, together with the description, serve to explain the principles of the disclosure. The drawings are only for the purpose of illustrating embodiments of the disclosure and are not to be construed as limiting the disclosure.

Figure 1:
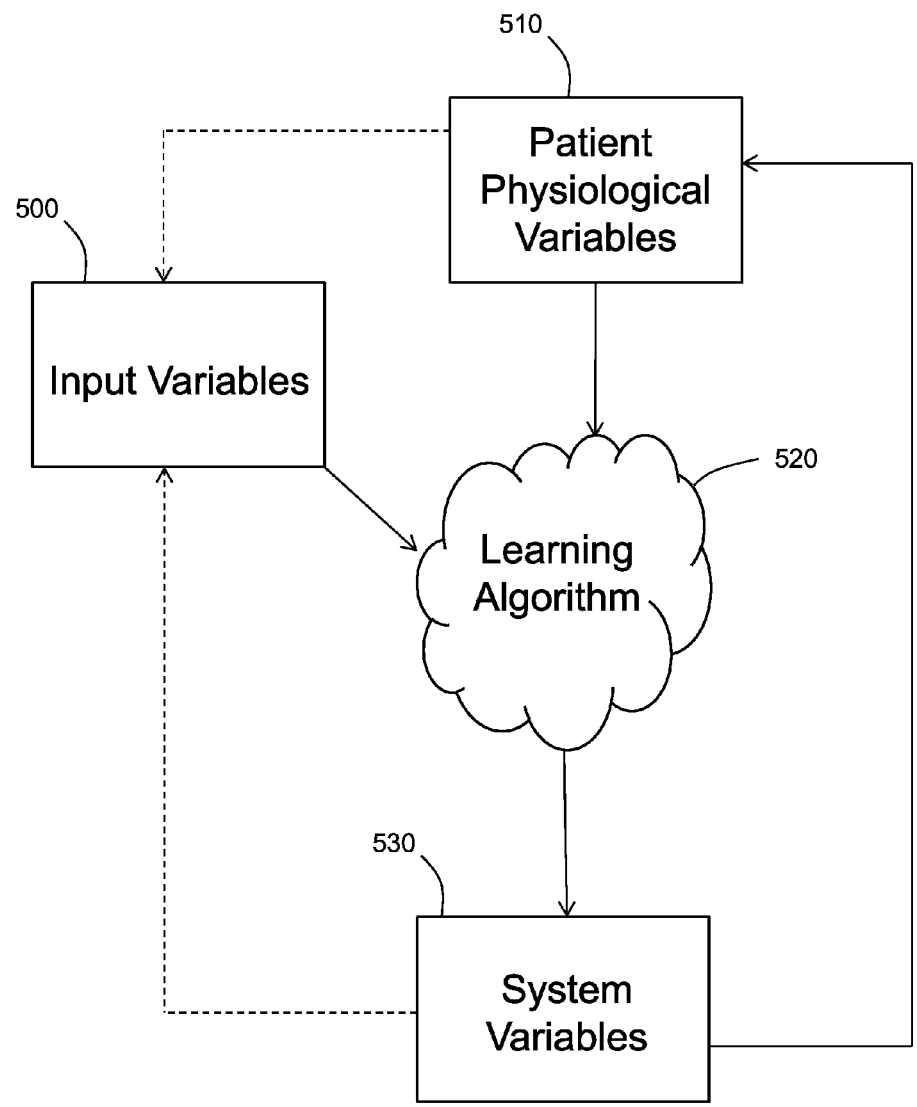
FIGS. 1-7 are flow diagrams illustrating methods in accordance with various embodiments described herein.

The schematic drawings presented herein are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar.

DETAILED DESCRIPTION

In the following detailed description, reference is made to the accompanying drawings that form a part hereof, and in which are shown by way of illustration several embodiments of devices, systems and methods. It is to be understood that other embodiments are contemplated and may be made without departing from the scope or spirit of the present disclosure. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise.

As used in this specification and the appended claims, the term "or" is generally employed in its sense including "and/or" unless the content clearly dictates otherwise.

As used herein, "have", "having", "include", "including", "comprise", "comprising" or the like are used in their open ended sense, and generally mean "including, but not limited to."

As used herein, a "patient for which a blood fluid removal session is indicated" is a patient that has undergone, is undergoing, or is likely to undergo at least one blood fluid removal session. In general, such patients are fluid overloaded patients, such as patients suffering from heart failure, chronic kidney disease, or acute kidney failure. Often such patients are stage 3 to stage 5 chronic kidney disease patients, are unresponsive or under-responsive to diuretics, or the like.

As used herein, a "blood fluid removal process," or the like, refers to a process from which fluid is removed from blood of a patient and the blood is returned to the patient. In most cases, the blood is also cleaned; i.e., waste products are removed from the blood and cleaned blood is returned to the patient. Examples of blood fluid removal processes include ultrafiltration, hemofiltration, hemodialysis, hemodiafiltration, peritoneal dialysis and the like. Any patient for which blood fluid removal is indicated may benefit from the devices, systems and methods described herein.

As used herein, "effective" or the like, as it relates to patient parameters, refers to the how close one or more patient parameters are to one or more target for the one or more parameters. Thus, a "most effective" patient parameter to date is a patient parameter at a given time that is closer to the target than the same parameter measured at any previous time. A "more effective" patient parameter is a parameter measured at a given time that is closer to the target than the same parameter measured at another time. A "least effective" patient parameter to date is a patient parameter at a given time that is farther from the target than the same parameter measured at any previous time. A "less effective" patient parameter is a parameter measured or observed at a given time that is farther from the target than the same parameter measured at another time.

This disclosure, among other things, describes devices, systems and methods for monitoring patient physiological parameters and blood fluid removal system parameters and identifying those system parameters that result in improved physiological parameters or in worsened physiological parameters. By comparing the patient's past responses to system parameters or changes in system parameters, a blood fluid removal system may be able to avoid future use of parameters that may harm the patient and may be able to learn which parameters are likely to be most effective in treating the patient in a blood fluid removal session.

U.S. Provisional Patent Application No. 61/480,539, entitled ADAPTIVE SYSTEM FOR BLOOD FLUID REMOVAL, filed on Apr. 29, 2011, is incorporated herein by reference in its entirety to the extent that it does not conflict with the present disclosure. While the present disclosure includes much of the discussion and drawings presented in U.S. Provisional Patent Application No. 61/480, 539, the present application enhances the disclosure with regard to inter-session parameters and learning.

Referring to FIG. 1, a high level schematic overview of embodiments of the present disclosure is shown. As shown in FIG. 1, a learning algorithm 520 is employed to determine what system parameters work well to produce desired patient physiological results based on input. Any suitable input variable 500 may be considered by the algorithm 520 in the learning process. For example, variables such as how long it has been since the patient's last blood removal session may be input. Such input could be important as patients undergoing, for example, hemodialysis on a Monday, Wednesday, Friday schedule are more likely to suffer an adverse cardiac event just before, during or after the Monday blood fluid removal session. Accordingly, the algorithm 520 may consider whether a different set of system parameters should be employed when the patient has not undergone a session in 72 hours relative to when the patient has not undergone a session in 48 hours. Input variables 500 may also include whether the patient has limited time to undergo a blood fluid removal session. The algorithm 520 can determine whether a faster fluid removal rate should be used or whether a partial session at a reduced fluid removal rate would likely be more effective based on the patient's history of response to fast fluid removal rates. Alternatively, the patient may have additional time to undergo a blood fluid removal session, and the algorithm 520 can take such input 500 into account to determine whether there may be an advantage to slower fluid removal rates or slower adjustment of a concentration of an electrolyte based on the patient's history. Of course, it will be understood that any other suitable input variables 500 may be entered regarding target outcomes (e.g., quick session, long session, etc.), patient history (e.g., time since last session), or the like. In embodiments, input that takes into account future patient behavior or needs may be entered into the system. For example, if a patient knows that they will miss a session or the time until their next session will be delayed from normal, time until next session may be entered, which may affect the system parameters (e.g., may remove additional fluid, etc.). By way of another example, if the patient knows that they will eat or drink an amount more than optimal before the session, expected consumption levels may be input in the system.

As shown in FIG. 1, the algorithm 520, based on input variables 500, and patient physiological variables 510 may determine appropriate system variables 530 to employ based on the patient's history with blood fluid sessions under the algorithm. During a blood fluid session, system variables 530 may be changed and the patient physiological response may be monitored in response to the changed system variables. If one or more of the patient's physiological variables 510 improve, the algorithm 520 can associate the changed system variables 530 with the improved patient outcome so that the changed system variables 530 may be used later in the session or in a future session when the patient has a similar set of physiological variables 510. If one or more of the patient's physiological variables 510 worsen, the algorithm 520 can associate the changed system variables 530 with a worsened patient outcome so that the changed system variables 530 may be avoided later in the session or in a future session when the patient has a similar set of physiological variables 510.

In embodiments, the input variables 500 include patient physiological variables that have occurred in a time period preceding a blood fluid removal session. For example, the time period may be a period of time (e.g., all or one or more portions of time) since the patient's last session. In embodiments, the input variables include input indicating (i) how long favorable patient variables 510 (e.g., above or below a predetermined threshold) were observed after the last session; (ii) the rate of change of patient variables 510 following the last session, (iii) etc., all of which may be compared against system parameters 530 used in the previous session. If the patient physiological 510 or other variables (e.g. patient input regarding how the patient has felt), were favorable since the last session, the system may employ similar variables in future sessions. It may also or alternatively be desirable to monitor patient physiological or other variables in a time period leading up to a session and input such variables into the algorithm 520 or system before the session. The system or algorithm 520 can then determine whether the patient has presented with similar symptoms or parameters in previous sessions and employ system variables 530 to which the patient responded favorably, either in the session, after the session, or both in the session and after the session. Accordingly, the system or algorithm 520 may monitor patient well-being, which may be derived from patient physiological variable 510 or input variables 500, within a session and between sessions to determine which system variables should be employed and changed based on the patient response to previous sessions. As indicated by the dashed lines and arrows in FIG. 1, patient physiological variables 510 obtained between sessions and system variables 530 used in a prior session may be input variables 500 in a current or upcoming session.

In embodiments, the physiological variables 510 are monitored by sensors that feed data regarding the variables directly into the algorithm 520 or electronics running the algorithm. The sensors may monitor fluid volume in the patient's blood; fluid volume in the patient's tissue; concentrations of electrolytes in the patient's blood; pH of the patient's blood; one or more cardiovascular parameter of the patient, such as blood pressure, heart rhythm, heart rate; or combinations or indicators thereof. The sensors may monitor the patient physiological parameters before, during or after a blood fluid removal session.

Any suitable senor may be employed. Examples of sensors and systems that may be employed with regard to blood fluid volumes and tissue fluid volumes are discussed in U.S. Provisional Patent Application No. 61/480,528, filed on Apr. 29, 2011, entitled FLUID VOLUME MONITORING FOR PATIENTS WITH RENAL DISEASE; and U.S. Provisional Patent Application No. 61/480,530, filed on Apr. 29, 2011, entitled MONITORING FLUID VOLUME FOR PATIENTS WITH RENAL DISEASE, which applications are hereby incorporated herein by reference in their respective entireties to the extent that they do not conflict with the present disclosure. Sensors for monitoring tissue fluid volume, blood fluid volume, fluid flow or volume diverted from blood and the like typically monitor fluid indirectly, and directly monitor an indicator of fluid volume, flow or the like. For example, a sensor may indirectly monitor hematocrit (the portion of the blood volume that is occupied by red blood cells). Any suitable hematocrit sensor, such as a CRIT-LINE monitor from HEMA METRICS (see, HEMA METRICS, CRIT-LINE hematocrit accuracy, Vol. 1, Techn Note No. 11 (Rev. D) Feb. 24, 2003), may be used and may serve as an indicator of blood fluid volume. A sensor configured to monitor hemoglobin levels may also be used as an indicator of blood fluid volume, as hemoglobin concentration is typically proportional to red blood cell concentration. Thus, lower the hemoglobin concentrations may be indicative of higher blood fluid volume. Any suitable sensor may be used to measure hemoglobin concentration, such as sensors used in pulse oximeters which measure adsorption of red and infrared light to determine concentration of oxygenated hemoglobin and deoxyhemoglobin, respectfully. The sensors (which may include the associated light source(s)) may be placed in any suitable location, such as around tubing that carries blood from the patient to the blood fluid removal device or from the blood fluid removal device to the patient, within the blood fluid removal device, or the like. In addition or alternatively, a sensor may be implanted in a patient and disposed about a blood vessel to measure hemoglobin levels, and thus hematocrit and blood fluid levels. By way of further example, total blood protein or albumin concentrations and blood pressure, alone or in combination, can be used to evaluate blood volume. High blood pressure combined with low hematocrit or low blood protein may indicate a higher possibility of blood fluid overloading. Alternatively or additionally, blood viscosity may be used as an indicator of blood fluid volume and may be measured by pressure or flow. Impedance, capacitance, or dialectic constant sensors may be employed to monitor fluid volume. For example, impedance may be monitored between two electrodes. The electrodes may be operably coupled to control and processing electronics via leads. The electronics are configured to generate a voltage differential between the electrodes, current may be measured, and impedance calculated. The measurement may be done in either DC or AC mode. Impedance or phase angle may be correlated to tissue fluid volume. Tissue impedance sensing for purposes of monitoring tissue fluid volume has been well documented. One example of a well studied system that may be used or modified for use herein is Medtronic, Inc.'s OptiVol® fluid status monitoring system. Such a system, or other similar systems, have well-documented procedures for determining acceptable ranges of tissue impedance and thus fluid volume. See, e.g., (i) Siegenthalar, et al. Journal of Clinical Monitoring and Computing (2010): 24:449-451, and (ii) Wang, Am. J. Cardiology, 99(Suppl):3G-1-G, May 21, 2007. Alternatively or in addition, tissue impedance may be monitored for a suitable period of time to establish as suitable baseline, and patient markers or clinician input may be used to instruct whether the patient is fluid overloaded or under-loaded. The data acquired by impedance sensor and input data regarding fluid status of the patient at the time the sensor data is acquired may be used to establish suitable ranges for impedance values.

Examples of sensors and systems for monitoring pH and electrolyte concentration are disclosed in U.S. Provisional Patent Application No. 61/480,532, filed on Apr. 29, 2011, entitled ELECTROLYTE AND pH MONITORING FOR FLUID REMOVAL PROCESSES, which application is hereby incorporated herein by reference in its entirety to the extent that it does not conflict with the present disclosure. Of course, any suitable sensor or systems for monitoring pH and electrolyte concentration may be used. For example, a transducer may be employed to detect pH or electrolytes. Suitable transducers may include an ion selective electrode configured to detect $H^+$ ions, $K^+$ ions, $Na^+$ ions, $Ca^{2+}$ ions, $Cl^-$ ions, phosphate ions, magnesium ions, acetate ions, amino acids ions, or the like. Such electrodes, and components of sensors employing such electrodes, are known in the art and may be employed, or modified to be employed, for use in the monitoring described herein. One or more sensors may be employed to detect one or more ions to gauge pH or electrolytes in the blood. In some embodiments, a sensor may have more than one transducer, even if leadless, that may monitor more than one ionic species. By measuring more than one ionic species, a more detailed understanding of the levels of various electrolytes or blood components may be had. For example, in some patients in some situations, one electrolyte may be at elevated levels while another may be at reduced levels. In some embodiments, more than one sensor for the same ion is employed for purposes of result confirmation and redundancy, which can improve reliability and accuracy. In some embodiments, sensors for the same ion may be configured to accurately detect different ranges of concentrations of the ion. In embodiments, more than one transducer is present in a single unit. This allows for convenient data collection and circuitry, as all the data may be collected in one place at the same time. Further, the multiple transducers may share the same fluid collection mechanism (e.g., a microdialyzer in the case of an implant), and if needed or desired, may share the same data processing and memory storage components. A sensor (or transducer) for detecting pH, electrolyte concentration, or the like may be placed at any suitable location for purposes of monitoring electrolytes or pH. For example, the sensor may be implanted in the patient, located external to the patient an upstream of a blood fluid removal device, located external to the patient and downstream of the blood fluid removal device, or the like.

Examples of sensors and systems for monitoring cardiovascular parameters are disclosed in U.S. Provisional Patent Application No. 61/480,535, filed on Apr. 29, 2011, entitled CARDIOVASCULAR MONITORING FOR FLUID REMOVAL PROCESSES, which application is hereby incorporated herein by reference in its entirety to the extent that it does not conflict with the present disclosure. Of course, any suitable sensor for monitoring cardiovascular parameters may be used. In embodiments, pH or electrolyte sensors; e.g., as described above, may be used to monitor cardiovascular parameters. Sensors for monitoring heart rate or heart rhythm may be used. One suitable implantable sensor device that is configured to monitor a patient's ECG signals is a Medtronic, Inc.'s Reveal® series insertable cardiac monitor. In embodiments, the sensor device may be a suitably equipped pacemaker or defibrillator already implanted in the patient. Monitored cardiac signals from such a device may be transmitted to a blood fluid removal device or intermediate device for use in the blood fluid removal session or for setting the prescription for the blood fluid removal session. Blood pressure monitors, which may be external or implantable (such as Medtronic Inc.'s active leadless pressure sensor (ALPS), which generally takes the form of a stent to anchor the device within a vessel, may be employed. Such a device may be placed in any suitable blood vessel location, such as in a femoral artery or pulmonary artery. A wearable sensor system, such as a Holter sensor system, may be used to monitor ECG activity of the patient. Regardless of whether the sensor or sensor system employed, or components thereof, is implantable, wearable, part of a larger stand-alone device, or part of a blood fluid monitoring device, the sensor may monitor any suitable cardiovascular parameter of a patient. In various embodiments, the sensors or monitoring systems are configured to monitor one or more of heart rate, heart rhythm or a variable thereof, or blood pressure. Examples of variables of heart rhythm that may be measured are heart rate variability (HRV), heart rate turbulence (HRT), T-wave alternans (TWA), P-wave dispersion, T-wave dispersion, Q-T interval, ventricular premature depolarization (VPD), or the like.

As indicated above, sensors for monitoring patient physiological parameters may be, or may have components that are, implantable or wearable. In embodiments, multiple sensors may be connected via telemetry, body bus, or the like. The connected sensors may be of the same or different type (e.g., pH or impedance). Such connected sensors may be placed (e.g., internal or external) for purposes of monitoring at various locations of the patient's body.

Monitoring may occur during a blood removal session or between blood removal sessions. In embodiments, blood fluid removal is chronically performed, such as when a blood fluid removal device or a component thereof is wearable or implantable, and monitoring is chronically performed. Chronic monitoring in association with blood fluid removal is described in U.S. Provisional Patent Application No. 61/480,544, filed on Apr. 29, 2011, entitled CHRONIC pH OR ELECTROLYTE MONITORING, which application is hereby incorporated herein by reference in its entirety to the extent that it does not conflict with the present disclosure.

Monitoring may alternatively or additionally include receiving patient or physician feedback regarding the patient's state. For example, the patient may indicate a point in time when cramping begins, which often happens when too much fluid is removed. The blood fluid monitoring device may include an input, such as a keyboard or touch screen display for entering such data. Alternatively, a separate device such as a patient programmer, laptop computer, tablet computer, personal data assistance, smart phone or the like may be used to input the data; or the like.

Any suitable system variable 530 may be adjusted. FIGS. 10-15, and the associated text below, describe some suitable blood fluid removal systems and variables that may be adjusted. In many cases, fluid removal rate, blood flow rate, or concentration of electrolyte or composition of pH buffer in replacement fluid or dialysate may be adjusted. It may be desirable to monitor blood fluid removal system parameters to ensure that the system is performing in an expected manner. For example, it may be desirable to monitor fluid rate removal rather than merely adjusting a system variable related to fluid removal rate to ensure that the adjusted system variable actually adjusted the fluid removal rate in the expected manner Any suitable system and method may be employed to monitor such system performance.

Examples of systems and methods for monitoring system performance are described in U.S. Provisional Patent Application No. 61/480,541, filed on Apr. 29, 2011, entitled BLOOD FLUID REMOVAL SYSTEM PERFORMANCE MONITORING, which application is hereby incorporated herein by reference in its entirety to the extent that it does not conflict with the present disclosure. For example, flow sensors such as an acoustic Doppler velocimeter, an optical flow meter, a thermal flow meter, a Venturi meter, in-fluid paddle type meter, or the like may be used upstream or downstream of blood fluid removal device to monitor system performance. Sensors configured to monitor an indicator of a compound in blood or in fluid removed from the blood may be used to monitor system performance. The sensors may be configured to monitor components of blood that are configured to be removed during some blood fluid removal processes, such as hemodialysis. Examples of such compounds include urea, creatinine, sulfate, phosphate, β-2-microglobulin, or the like. Sensors capable of measuring such compounds are known in the art and can be readily adapted for used herein. For example, Nova Biomedical manufactures a variety of sensors capable of detecting components in blood such as creatinine, phosphate, urea and the like, which sensors can be employed or adapted for use herein. Other urea sensor detection technology that may be employed or adapted for used herein is described by Zhong et al., Clin. J. Biotechnol. 1992; 8(1):57-65. β-2-microglobulin sensor detection technology that may be employed or adapted for used herein is described by Brynda et al., Biosens Bioelectron. 1999; 14(4):363-8 and by Nedelkov et al., Proteomics. 2002; 2(4):441-6. Of course, any suitable sensor technology may be employed. By way of further example, pressure sensors may be employed to monitor pressure differential across a blood fluid removal membrane to monitor system performance.

Figure 2:
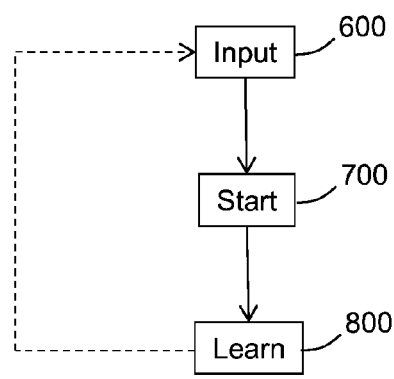

Referring now to FIG. 2, a high level flow diagram of a method is described. The method includes providing input (600), such as input variables discussed above with regard to FIG. 1, to a blood fluid removal system. The method also includes initiating or starting (700) a blood fluid removal session, and learning (800) from the session. The learning (800) may be as discussed above with regard to FIG. 1 with system parameters being varied and patient physiological parameters being monitored to determine which system parameter adjustments result in desirable patient physiologic outcomes. The learning may also occur over multiple sessions by monitoring patient variables within the sessions or by monitoring patient variables between sessions to determine how well the patient responded prior sessions to predict how well a patient will respond to future sessions (or to set initial parameters for future sessions based on prior experiences).

Figure 3A:
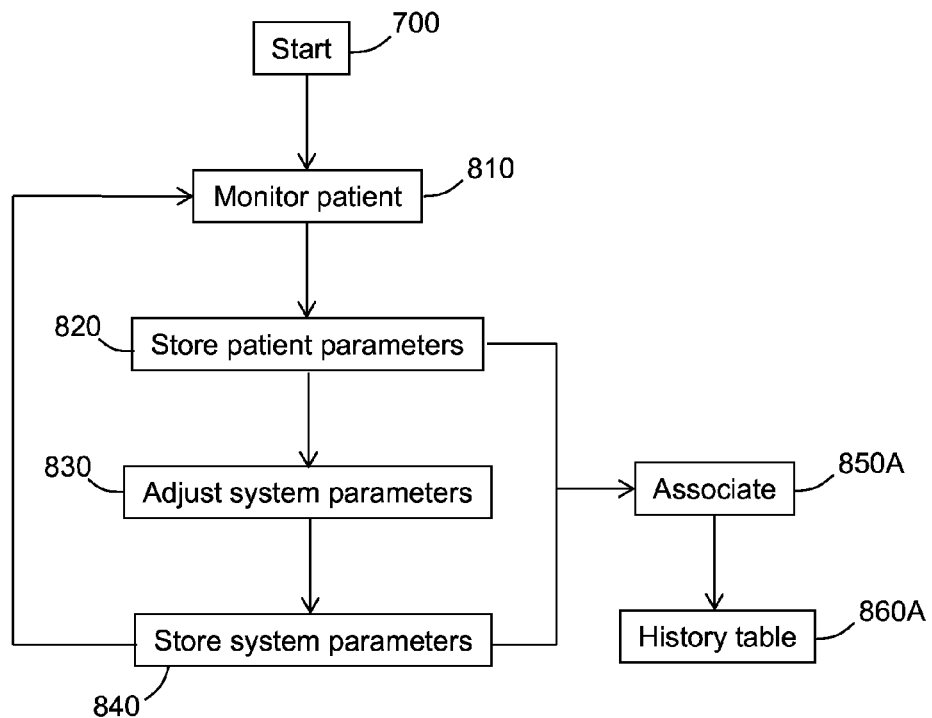

For example and with reference to FIG. 3A, additional detail regarding an embodiment of a learning process that may occur during a blood fluid removal session is shown. The blood fluid removal session is started (700) and the patient is monitored (810). Monitored patient parameters, such as patient physiological variables as discussed above, are stored (820); e.g., in memory of the blood fluid removal system. The system parameters, such as system variables described above, which may include rate of fluid removal from the blood or electrolyte concentration of a dialysate or replacement fluid, are adjusted (830) and the system parameters are stored (840); e.g., in memory of the blood fluid removal system, and patient monitoring (810) continues. The set of stored patient parameters (820) are associated (850A) with a set of stored system parameters (840) so that the system may recall particular system parameters that were employed at the time the patient had a given set of parameters. The data regarding the stored patient parameters (820) and the stored system parameters (840) may be tagged with, for example, a time event to associate the two sets of data. Of course any other suitable method or mechanism for associating the data sets may be employed. In some embodiments, the associated data, or a portion thereof, is placed in a lookup table tracking the patient's history of physiological response to changing system parameters (860A).

Figure 3B:
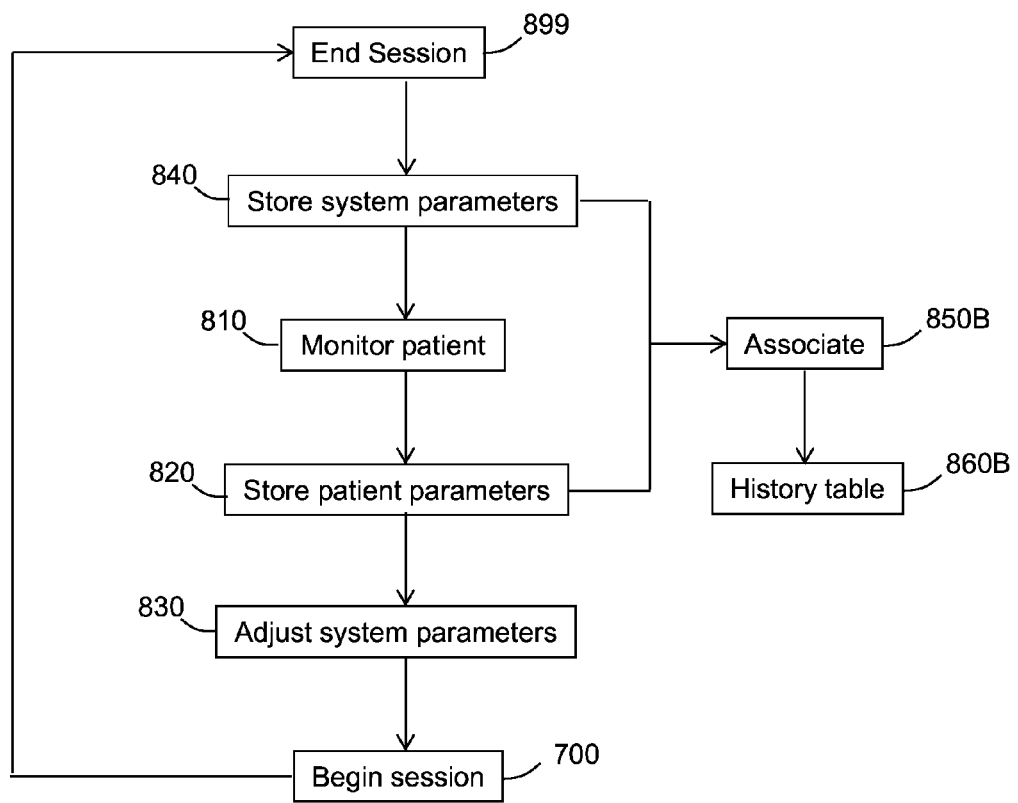

Referring now to FIG. 3B, an overview of a learning process that may occur with monitoring between blood fluid removal sessions is shown. Before, during or after a blood fluid removal session is ended (899), system parameters used in the session are stored (840). The system parameters, such as system variables described above, which may include rate of fluid removal from the blood or electrolyte concentration of a dialysate or replacement fluid, as well as any adjustments made during the session that has just ended may be stored in memory and associated with the patient. During one or more time periods between the end of the session (899) and the start of the next session (700), the patient is monitored (810). Monitored patient parameters, such as patient physiological variables as discussed above, are stored (820); e.g., in memory of the blood fluid removal system or in memory of a device capable of communicating with, or a part of, the blood fluid removal system. For example, if monitoring (810), or a portion thereof, occurs via an implanted device, the implantable monitoring device may be configured to wirelessly communicate with a blood fluid removal system or a device capable of communicating with the blood fluid removal system. If monitoring includes assays or other diagnostic procedures for which data is presented to a user, such as a health care provider, the data may be entered into a blood fluid removal system or device in communication with the blood fluid removal system. The set of stored system parameters (840) are associated (850B) with a set of patient system parameters (820) so that the system may recall particular system parameters that were employed in prior sessions that resulted in a given set of patient parameters. The data regarding the stored patient parameters (820) and the stored system parameters (840) may be tagged with, for example, a time event to associate the two sets of data. Of course any other suitable method or mechanism for associating the data sets may be employed. In some embodiments, the associated data, or a portion thereof, is placed in a lookup table tracking the patient's history of physiological response to system parameters (860B). Depending on the patient's response (patient monitoring 810) to the prior sessions, the system parameters may be adjusted (830) prior to beginning the next session (700). The patient's responses between sessions may also affect changes made during a session.

Figure 3C:
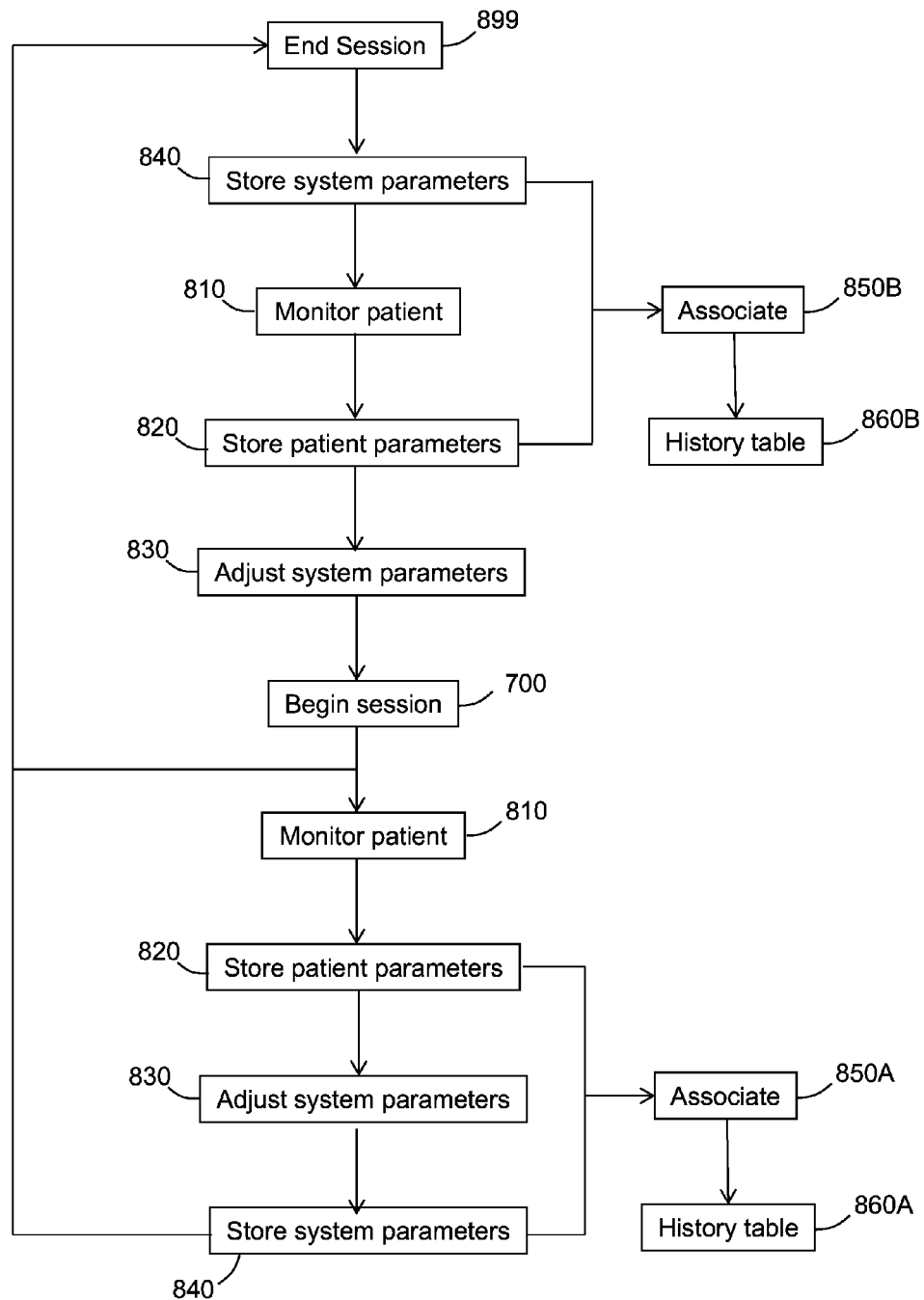

Referring now to FIG. 3C, an overview of a learning process that accounts for both inter-session and intra-session patient monitoring is shown. The process depicted in FIG. 3C is mainly a composite of the processes depicted and described above with regard to FIGS. 3A-B. As depicted in FIG. 3C, the process or algorithm may include associating (850A) system parameters (840), and adjustments thereof (830), that result in good or bad outcomes with regard to patient parameters (820) and may recall those associations for later use, e.g. in the form of a lookup table (860A) for purposes of making future adjustments to system parameters (830) based on patient response (810) within a session. Prior patient responses occurring between prior sessions (i.e., between end of session 899 and beginning of session 700) may also be taken into account (e.g., associated parameters (850B) that include patient parameters obtained between sessions) by, for example, referring to lookup table 860B. If, for example, changes in systems parameters (830) within a session are associated with good (effective) or bad (ineffective) patient responses (810) between sessions, similar changes may be made or avoided, as relevant, within a session. In addition, the patient response (810) to a prior session or the patient's condition (810) before a session may warrant adjustment of system parameters (830) prior to beginning a session (700). The patient response (810) within prior sessions may also be taken into account (e.g., by reference to history table 860A) in making system adjustments prior to beginning a session.

Figure 4A:
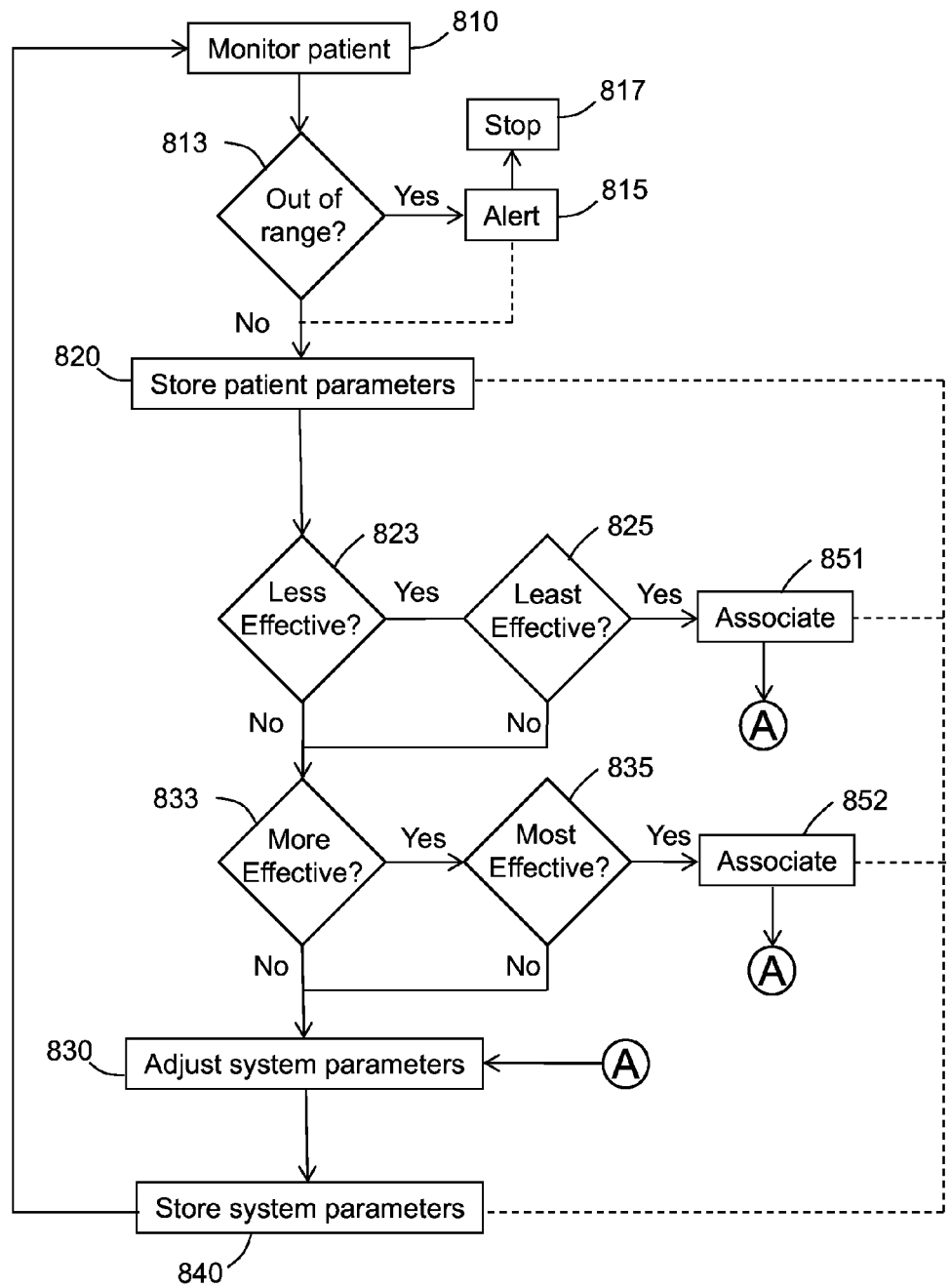

A more detailed embodiment of a within-session learning algorithm, or method is presented in FIG. 4A. In the embodiment depicted in FIG. 4A, patient is monitored (810) during a blood fluid removal session. It may be desirable to determine whether data acquired from patient monitoring is out of range (813). As used herein, "out of range" means that a value of a monitored parameter exceeds (ie., is above or below) a predetermined range of values. The predetermined range of values may be indicative of a patient safety concern. If the data is out of range, an alert may be issued (815) or the session may be stopped (817). In some cases, it may be desirable to continue with the session, even if the monitored data, or some aspect thereof is out of range. In the depicted embodiment, if the session is continued, (e.g., due to choice or to the monitored data not being out of range), data regarding the monitored patient parameters is stored (820) and is compared to stored patient data previously obtained (e.g., in a prior session or earlier in the session). A determination may be made as to whether the present patient parameter data is less effective (823) than stored patient parameter data resulting from system parameter adjustments (830) that occurred just prior to the current set of system parameters. If the data is determined to be less effective (823), the stored current patient parameters (820) may be associated (851) with stored current system parameters (840); e.g., as discussed above. In some cases, it may be desirable to determine whether the current patient parameter data, or a portion or aspect thereof, is the least effective that has been detected in the patient in a current or previous blood fluid removal session (825); e.g. by comparing the current patient data to a history of collected patient data. If the current patient data is the least effective observed (825) to date, the stored current patient parameters (820) may be associated (851) with stored current system parameters (840). In this way, only the "least effective" patient conditions are tracked, as opposed to all patient conditions, which can save on memory and processing power. In any case, once the patient and system parameter data is associated (851), the system parameters may be adjusted (830) and the process repeated.

If the present patient parameter data is determined to not be less effective than stored patient parameter data resulting from system parameter adjustments that occurred just prior to the current set of system parameters, a determination may be made as to whether the present patient parameter data is more effective (833) than stored patient parameter data resulting from system parameter adjustments (830) that occurred just prior to the current set of system parameters. If the data is determined to be more effective (833), the stored current patient parameters (820) may be associated (852) with stored current system parameters (840); e.g., as discussed above. In some cases, it may be desirable to determine whether the current patient parameter data, or a portion or aspect thereof, is the most effective that has been detected in the patient in a current or previous blood fluid removal session (835); e.g. by comparing the current patient data to a history of collected patient data (e.g., "history table" in FIG. 3). If the current patient data is the most effective observed (835) to date, the stored current patient parameters (820) may be associated (852) with stored current system parameters (840). In this way, only the "most effective" patient conditions are tracked, as opposed to all patient conditions, which can save on memory and processing power. In any case, once the patient and system parameter data is associated (852), the system parameters may be adjusted (830) and the process repeated.

Figure 4B:
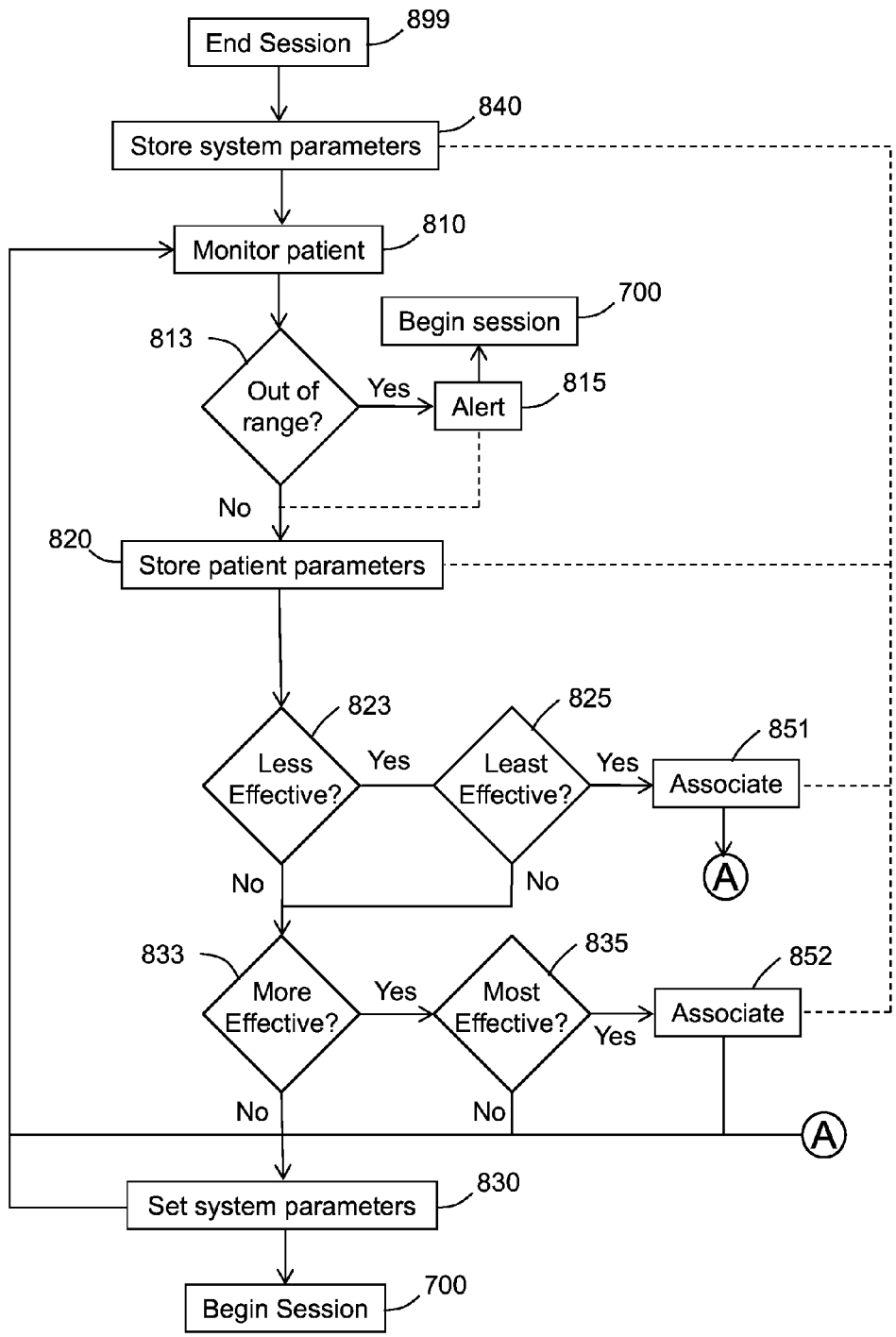

A more detailed embodiment of a between-session learning algorithm, or method is presented in FIG. 4B. In the embodiment depicted in FIG. 4B, patient is monitored (810) between a blood fluid removal sessions. It may be desirable to determine whether data acquired from patient monitoring (810) is out of range (813). If the data is out of range, an alert may be issued (815) prompting the patient to seek medical attention or prompting a health care or an implanted system or device to take action. In some cases, a new session may be begun (700) if patient conditions warrant. If a new session is not initiated, the inter-session process may continue. In the depicted embodiment, if the process is continued, data regarding the monitored patient parameters is stored (820) and is compared to stored patient data previously obtained (e.g., between prior sessions). A determination may be made as to whether the present patient parameter data is less effective (823) than stored patient parameter data obtained between previous sessions. If the data is determined to be less effective (823), the stored current patient parameters (820) may be associated (851) with stored system parameters (840) from the previous session that had ended (899). In some cases, it may be desirable to determine whether the current patient parameter data, or a portion or aspect thereof, is the least effective that has been detected in the patient between blood fluid removal sessions (825); e.g. by comparing the current patient data to a history of collected patient data. If the current patient data is the least effective observed (825) to date, the stored current patient parameters (820) may be associated (851) with stored system parameters (840) from the previous session that had ended (899). In this way, only the "least effective" patient conditions are tracked, as opposed to all patient conditions, which can save on memory and processing power. In any case, once the patient and system parameter data is associated (851), a recommendation as to system parameters to be used in the next session may be made (e.g., the system parameters for the future session may be set 830 based on the patient response or prior patient responses) may be adjusted (830) and the process repeated until the next session begins 700.

If the present patient parameter data is determined to not be less effective than stored patient parameter data obtained from time periods between prior sessions, a determination may be made as to whether the present patient parameter data is more effective (833) than stored patient parameter data obtained from between prior sessions. If the data is determined to be more effective (833), the stored current patient parameters (820) may be associated (852) with stored current parameters (840) from the previous session that had ended (899). In some cases, it may be desirable to determine whether the current patient parameter data, or a portion or aspect thereof, is the most effective that has been detected in the patient in a time between sessions (835); e.g. by comparing the current patient data to a history of collected patient data (e.g., "history table" in FIG. 3). If the current patient data is the most effective observed (835) to date, the stored current patient parameters (820) may be associated (852) with stored system parameters (840) from the previous session that had ended (899). In this way, only the "most effective" patient conditions are tracked, as opposed to all patient conditions, which can save on memory and processing power. In any case, once the patient and system parameter data is associated (852), recommendation system parameters may set (830) based on the patient response or prior patient responses, and the process repeated until the next session begins 700.

It will be understood that the processes or algorithms depicted in, and discussed above with regard to, FIGS. 4A-B may be combined (e.g., in a manner similar to the combination of FIGS. 3A and 3B into FIG. 3C). In this way, setting of system parameters for an upcoming session may take into account how a patient responded to such parameters within prior sessions, or altering of system parameters within a session may take into account how a patient responded to such alterations between prior sessions.

Figure 5A:
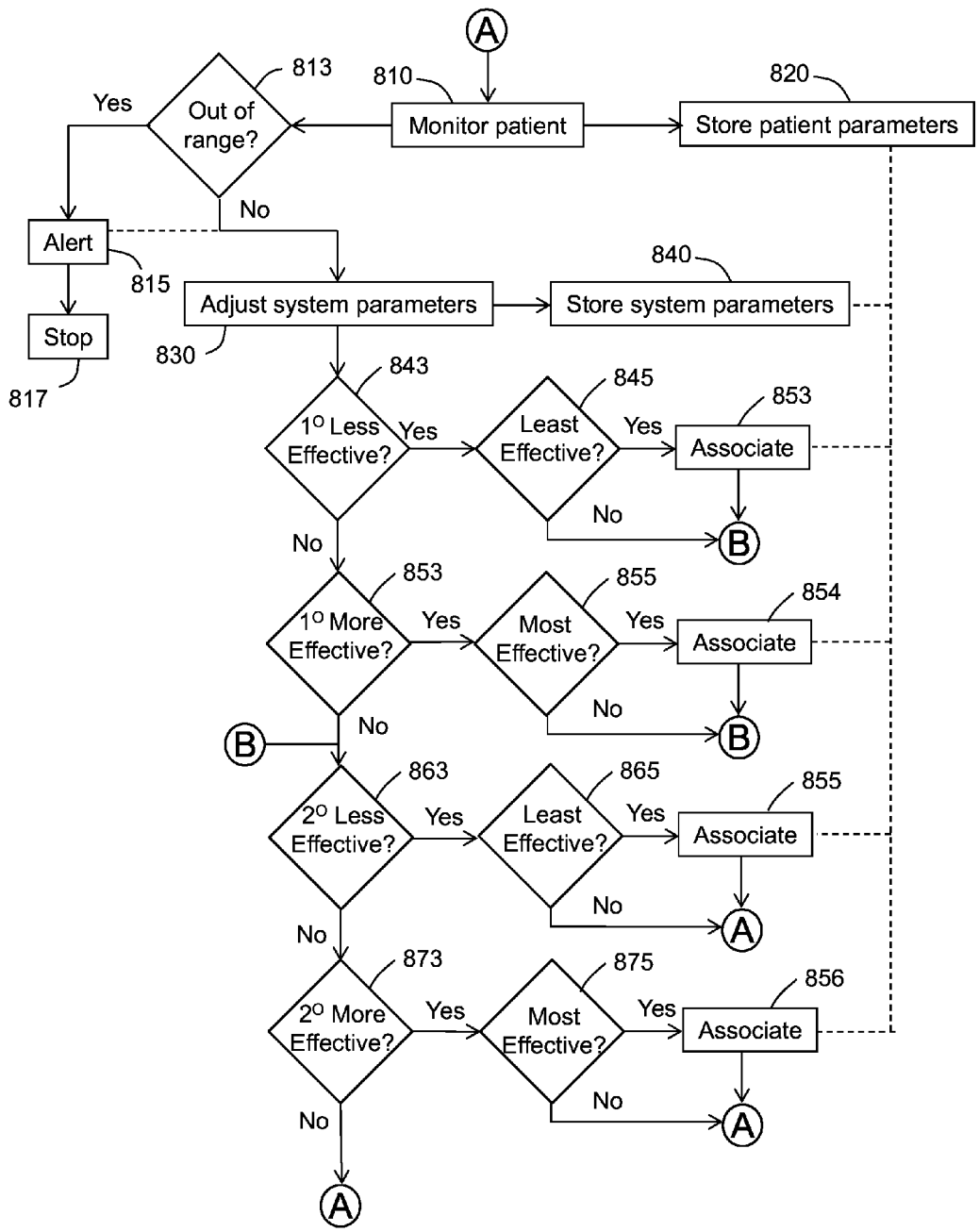

Referring now to FIG. 5A, an embodiment of a method where more than one patient parameter variable is evaluated in a manner similar to that described with regard to FIG. 4A. In the embodiment depicted in FIG. 5A, two patient parameter variables are evaluated. However, it will be understood that any number of patient parameter variables may be evaluated by employing a method as depicted in FIG. 5A or using any other suitable method. In the embodiment depicted in FIG. 5A, the variables are labeled "primary" and "secondary", as it may be desirable to prioritize patient parameter variables. For example, in some cases it may be desirable to monitor blood pressure and attempt to achieve a stable blood pressure at or near a target range throughout the session because hypotension is one of the most common side effects of blood fluid removal sessions. That is, as long as other patient parameters are not out of a pre-determined range, the system may attempt to keep blood pressure in check and make adjustments to that end. However, in some cases, reducing arrhythmias is the primary goal, as many patients for which a blood fluid removal process is indicated dire from complications due to arrhythmias. If arrhythmias are determined to be the primary patient parameter, the blood fluid removal system may attempt to keep arrhythmias in check and make adjustments to this effect without regard to other patient parameters, e.g., as long as the other patient parameters remain within acceptable limits.

The method depicted FIG. 5A includes monitoring patient parameters (810) (at least a primary and secondary patient parameter), storing patient parameter data (820), and determining whether a parameter, or aspect thereof, is out of a predetermined range (813). If the parameter is out of range, an alert may be issued (815), the blood fluid removal session may be stopped (817) or the session may continue. If the parameters are determined to not be out of range (813), the system parameters may be adjusted (843) and stored (840). A determination may then be made as to whether the primary patient parameter is less effective (843), e.g. by comparing current patient parameter data to stored patient parameter data resulting from system parameter adjustments that occurred just prior to the current set of system parameters. If the primary patient parameter is determined to be less effective (843), the current stored patient parameter data may be associated (853) with the current stored system parameters. Alternatively or in addition, a determination may be made as to whether the current patient parameter data regarding the primary parameter is the least effective that has been detected in the patient in a current or previous blood fluid removal session (845); e.g., as discussed above with regard to FIG. 4A. If it is the least effective, the current stored patient parameter data may be associated (853) with the current stored system parameters as described above with regard to FIG. 4A. Similarly determinations as to whether the primary patent parameter data is more effective (853) or the most effective to date (855) may be made and stored system and patient parameters may be associated (854). Similar determinations regarding whether the secondary patient parameter, or a value associated therewith, is less effective (863), the least effective (865), more effective (873), the most effective (875) and appropriate associations (855, 856) may be made. In this manner, the system may identify and learn how system parameters may affect individually monitored patient parameters, such as blood pressure, heart rate, fluid volume, and electrolyte concentration. Based on this information, the system may make choices as to which system parameters may be employed to produce results that are likely to be favorable to the patient.

Figure 5B:
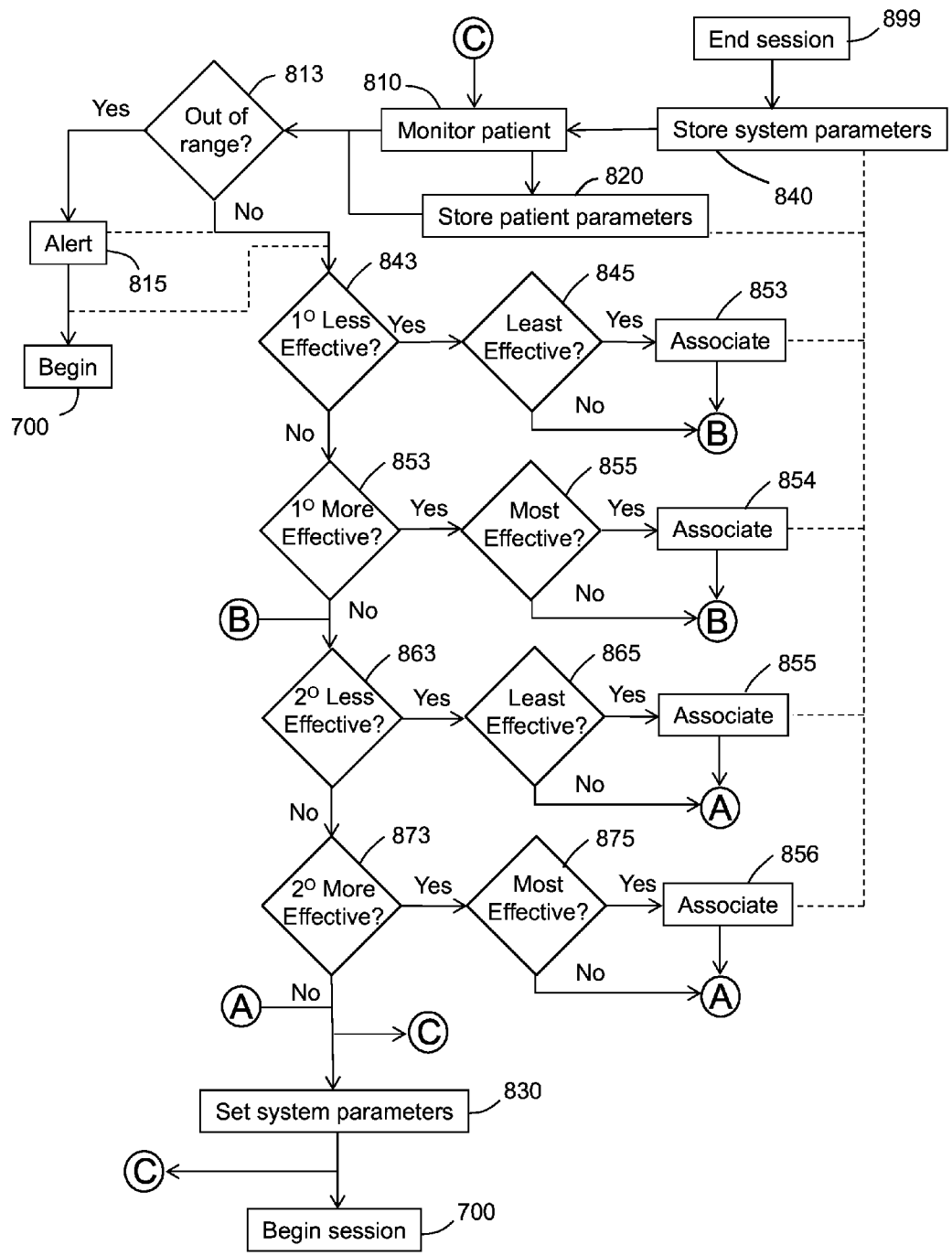

Referring now to FIG. 5B, an embodiment of a method where more than one patient parameter variable is evaluated between blood fluid removal sessions in a manner similar to that described with regard to FIG. 4B. In the embodiment depicted in FIG. 5B, two patient parameter variables are evaluated. However, it will be understood that any number of patient parameter variables may be evaluated by employing a method as depicted in FIG. 5B or using any other suitable method. In the embodiment depicted in FIG. 5B, the variables are labeled "1°" and "2°". However, such labeling does not necessarily imply that one variable is more important than another. While one variable may, in some circumstances be considered more important, the labeling of "primary" and "secondary" may merely imply that the variables being monitored and tracked are different from one another.

The method depicted FIG. 5B includes ending a blood fluid removal session (899) and storing system parameters (840) from the ended session, which may be done during the session or after the session has ended (as depicted). The method also includes monitoring patient parameters (810) (at least a primary and secondary patient parameter), storing patient parameter data (820), and determining whether a parameter, or aspect thereof, is out of a predetermined range (813). If the parameter is out of range, an alert may be issued (815), prompting the patient to seek medical attention or prompting a healthcare provider or system or device to take action. In some cases, a blood fluid removal process may be initiated (700), e.g. if warranted or desired. If the parameters are determined to not be out of range (813) or if a blood fluid session is not initiated, a determination may be made as to whether the primary patient parameter is less effective (843), e.g. by comparing current patient parameter data to stored patient parameter data resulting from system parameters used in the previous session. If the primary patient parameter is determined to be less effective (843), the current stored patient parameter data may be associated (853) with the stored system parameters from the previous session. Alternatively or in addition, a determination may be made as to whether the current patient parameter data regarding the primary parameter is the least effective that has been detected in the patient between blood fluid removal sessions (845); e.g., as discussed above with regard to FIG. 4B. If it is the least effective, the current stored patient parameter data may be associated (853) with the stored system parameters as described above with regard to FIG. 4B. Similarly determinations as to whether the primary patent parameter data is more effective (853) or the most effective to date (855) may be made and stored system and patient parameters may be associated (854). Similar determinations regarding whether the secondary patient parameter, or a value associated therewith, is less effective (863), the least effective (865), more effective (873), the most effective (875) and appropriate associations (855, 856) may be made. In this manner, the system may identify and learn how system parameters employed in previous sessions may affect individually monitored patient parameters, such as blood pressure, heart rate, fluid volume, and electrolyte concentration. Based on this information, the system may make choices as to which system parameters may be employed in future sessions to produce results that are likely to be favorable to the patient.

As depicted in FIG. 5B, recommended system parameters may be set (830) based on how the patient responded to the prior session or the patient's condition prior to the upcoming session. The recommended system parameters may be adjusted or set (830) more than once during the process of monitoring the patient between sessions or at the end of the inter-session monitoring before initiating the next blood fluid removal session (700).

It will be understood that the processes or algorithms depicted in, and discussed above with regard to, FIGS. 5A-B may be combined (e.g., in a manner similar to the combination of FIGS. 3A and 3B into FIG. 3C). In this way, setting of system parameters for an upcoming session may take into account how a patient responded to such parameters within prior sessions, or altering of system parameters within a session may take into account how a patient responded to such alterations between prior sessions.

Figure 6A:
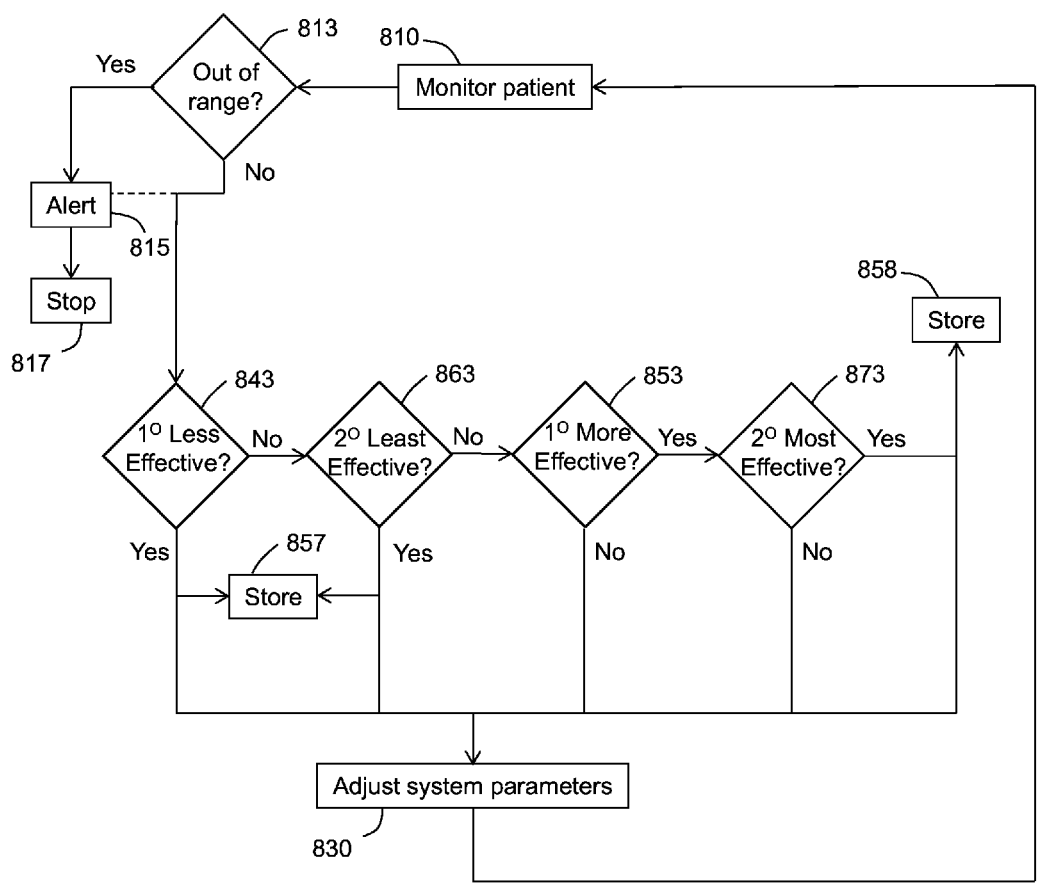

Referring now to FIG. 6A, a flow diagram depicting a process where the combined response of two or more patient parameters to changes in system parameters (830) is tracked within a session. For the purposes of convenience some of the steps depicted and described above with regard to FIGS. 4A and 5A are omitted from FIG. 6A. However, it will be understood that the same or similar steps may be employed with regard to the method depicted in FIG. 6A. In the depicted embodiment, patient parameters and system parameters are stored (857, 858) only when both the primary and secondary patient parameters are determined to become less effective (843, 863) or more effective (853,873). In this manner, the system may identify or learn which system parameters result in desirable (or undesirable) changes in multiple patient parameters.

Figure 6B:
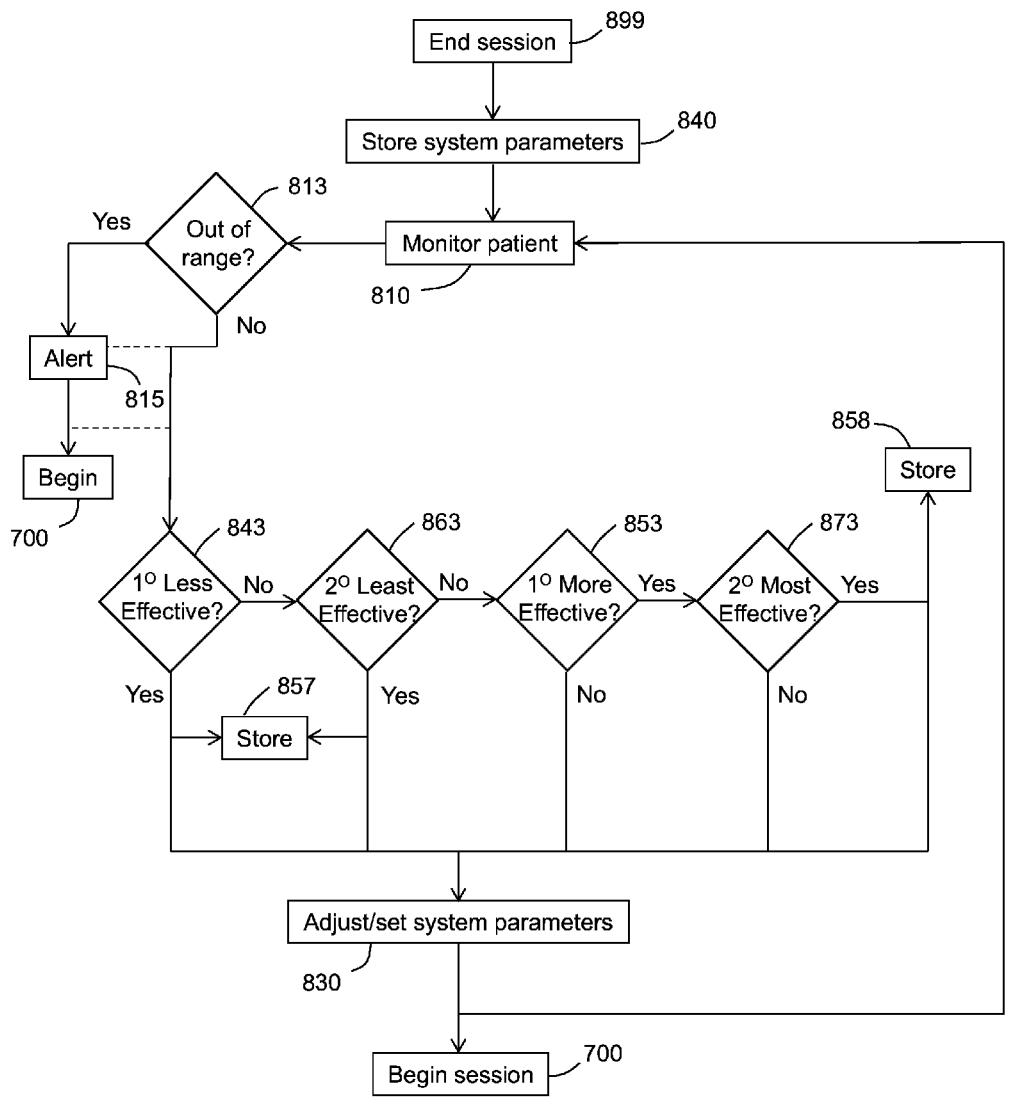

Referring now to FIG. 6B, a flow diagram depicting a process where the combined response of two or more patient parameters to changes in system parameters (830) is tracked between sessions. For the purposes of convenience some of the steps depicted and described above with regard to FIGS. 4B and 5B are omitted from FIG. 6B. However, it will be understood that the same or similar steps may be employed with regard to the method depicted in FIG. 6B. In the depicted embodiment, patient parameters are stored (857, 858) only when both the primary and secondary patient parameters are determined to become less effective (843, 863) or more effective (853,873) and may be associated with stored system parameters (840) for the previously ended session (899). In this manner, the system may identify or learn which system parameters result in desirable (or undesirable) changes in multiple patient parameters.

Through the association of patient parameter data and system parameter data as shown in FIGS. 3-6 and discussed above, a history of patient responses, within sessions or between sessions, to changing system parameters may be obtained. This history, which may be in the form of one or more lookup table, may be consulted prior to or during a blood fluid removal session to determine which system parameters, given the patient's physiological parameters at a given point in time, are more likely to cause the patient to respond favorably and which system parameters are more likely to cause the patient to respond negatively. Accordingly, the system may respond by adjusting or setting parameters to those that are more likely to cause the patient to respond favorably.

Figure 7:
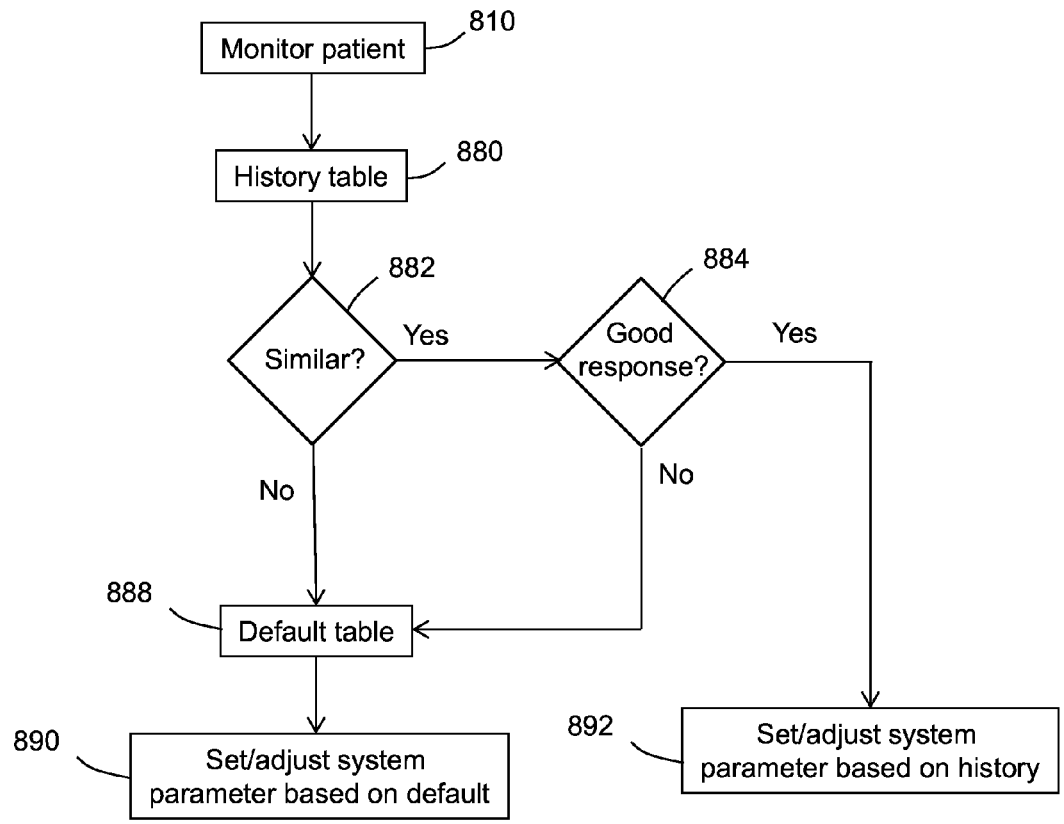

For example and with reference to FIG. 7, a flow diagram is shown that depicts and embodiment of how stored and associated data (e.g., as discussed above with regard to FIGS. 3-6) may be used to determine which system parameters to use at a given time in or before a blood fluid removal session. The method includes monitoring patient parameters (810), within a blood fluid removal session or between sessions, and consulting history lookup table (880), which may be generated by associating system parameters and patient parameters as described above with regard to FIGS. 3-6. Monitoring the patient (810) may include monitoring physiological variables or receiving input from the patient, a healthcare provider, or the like. A value associated with the current patient parameter data (obtained from monitoring 810) is compared to data regarding a corresponding value in the lookup table, and a determination is made as to whether the current patient parameter is similar to prior patient parameter data stored in the history table (882). By way of example, a value of a current patient parameter data set may be determined to be similar to a corresponding value in the lookup table if the values are within 10%. The system may consult the lookup table to identify the closest corresponding value, if more than one corresponding value is within the predetermined cutoff for being considered similar (e.g., within 10%). As used herein, a "corresponding" value is a value of the same parameter obtained at different times. The value may be a magnitude, a rate of change, an average, or the like. The parameter may be blood pressure, heart rate, fluid volume, concentration of electrolyte, or the like.

If more than one parameter or value of a parameter is compared to data in the lookup table, the system may determine whether each value for each parameter is within the predetermined cutoff for being considered similar and identify a prior patient parameter data set as being most similar by prioritizing or weighting parameters or by summing the percent differences between all of the current values and the corresponding values in the lookup table.

Regardless of how the system determines whether a current patient parameter data set is similar, or most similar, to a prior patient data set stored in the history table, a determination may be made as to whether the patient's response to the system parameters associated with the stored patient parameter data table was a favorable response (884); e.g., was "more effective" or "most effective" as discussed above with regard to FIGS. 4-6. If the prior patient response was determined to be a good response, the system parameters may be set or adjusted according to the parameters stored in the lookup table (892). If the prior patient response was considered to not to be similar (882) or good (884), a default table may be consulted (888) which contains non-patient specific system parameters that would generally be considered suitable in general circumstances or that would be considered suitable for a patient presenting with the current physiological parameters. The system parameters may then be set or adjusted according to the parameters stored in the default table (890).

It will be understood that prior patient negative responses (e.g., "less effective", "least effective to date") may be stored in a lookup table, accessed and used in a similar manner to that described with regard to the "good" responses in FIG. 7. In some embodiments, separate lookup tables are maintained for "more effective" responses (e.g., an "increased effectiveness" data table) and for "less effective responses" (e.g., a "decreased effectiveness" data table). In some embodiments, the "increased effectiveness" lookup table and the "decreased effectiveness" lookup table are the same data table, which stores patient parameters and associated system parameters that resulted in "more effective", "most effective", "less effective" or "least effective" patient parameters. As discussed above, lookup tables may include information regarding patient data obtained within a session or between sessions.

Figure 8:
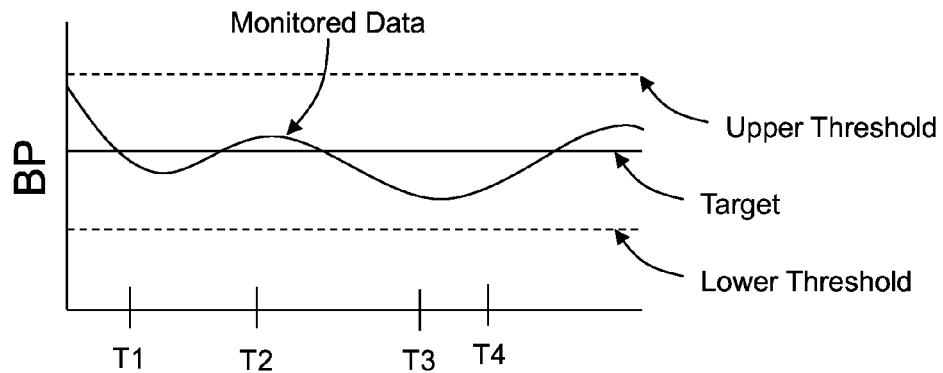
FIG. 8 is a schematic graphical representation of monitored data (not actual data) shown for purposes of illustration.
Figure 8:
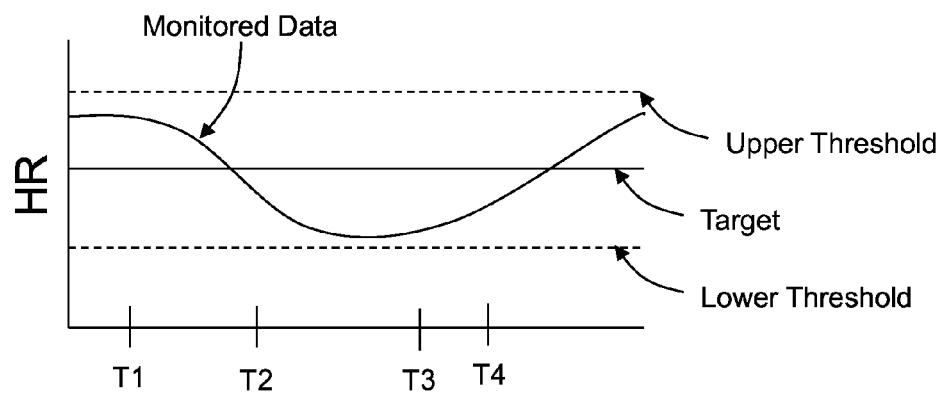
Figure 8:
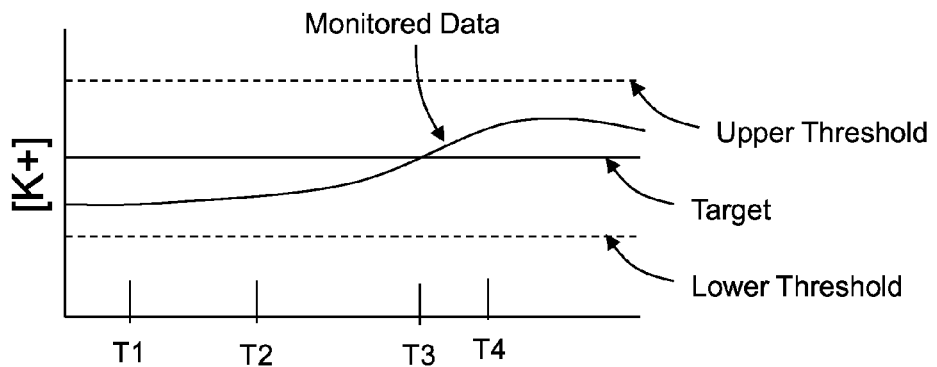

For purposes of example and to provide some clarity with regard to how one (or a blood fluid removal system) may determine whether patient parameter data is "out of range", "more effective", "less effective", and the like (e.g., as discussed above with regard to FIGS. 4-6), graphical schematic data is presented in FIG. 8 showing representations of monitored data (not actual data) for blood pressure (BP), heart rate (HR), and potassium concentration in the patient's blood ([K$^+$]). In the schematic illustration, a blood fluid removal session is initiated at T1 and is ended at T4. System parameters are changed at times T2 and T3. The patient parameters (BP, HR, [K$^+$]) are shown as changing in response to the changes in blood fluid removal system parameters and continuing to change after the session ends. As shown, not all patient parameters will respond similarly (e.g., more effective or less effective) in response to a system parameter change or session. In the depicted schematic illustrations, a desired target value is shown for each patient parameter. If the monitored data value achieves or approaches the target, a determination may be made that the change in system parameter or an overall session resulted in an increased effectiveness or "more effective" state for that parameter. If the monitored data value deviates from the target, a determination may be made that the change in system parameter or overall session parameters resulted in a decreased effectiveness or "less effective" state for that parameter. It will be understood that the timing of the patient parameter response to a change in system parameters may vary greatly from patient parameter to patient parameter. In some cases, changes in a patient parameter may be observed within seconds or minutes of a change in a system parameter. In other cases, a change in a patient parameter in response to a change in a system parameter may take hours or more to be fully appreciated or observed.

In the graphical depictions of the represented monitored data presented in FIG. 8, a lower threshold value and an upper threshold value are depicted by horizontal dashed lines. If the monitored data for a patient parameter exceeds the upper threshold value or crosses below the lower threshold value, a determination may be made that the value for that parameter is "out of range."

It will be understood that the condition of a patient may deteriorate with time, which is typical of patients having chronic kidney disease. Accordingly, the targets and upper and lower thresholds may vary with time. These targets and thresholds may be modified by input from, for example, a healthcare provider from time to time based on, e.g., the patient's health or status of patient parameters. Alternatively, the system may automatically adjust target or threshold values over time based on population data or based on data of a particular patient indicative of a generally deteriorating condition. If the target or thresholds are adjusted to or near predetermined cutoff values, an alert may be issued to that effect.

Further, target and threshold values for one or more parameters may be modified on a session-by-session basis. For example, if the patient is excessively fluid overloaded prior to a given session, the target or threshold tissue fluid levels may be adjusted upward for the next or current session. The negative consequences of too much fluid removal in one session or at too fast of a rate may outweigh the negative consequences of higher fluid levels remaining in the patient. Additional or more frequent fluid removal sessions may be employed to return the patient to more desirable fluid levels.

As shown in the examples presented in FIG. 8, the patient parameters change over time. In embodiments, values of one or more patient parameters are averaged over a period of time to account for fluctuations that may occur. The averaged value may be compared to the target and thresholds for determining whether a patient is improving. By averaging values over time, the effect of an anomalous value that may deviate significantly from the target value or may be out of bounds may be diminished. Of course, thresholds may be set for single occurrences, for example if the values of those occurrences may present an imminent health concern to the patient. In embodiments, the presence a single occurrence that deviates significantly from other recent occurrences may result in activation of a subroutine or monitoring method for detecting similar subsequent deviations. In embodiments, consecutive significant deviations, a percent of significant deviations within a given number of samples, or the like, may result in activation or an alert or alarm.

In embodiments, patient parameters are measured or monitored within discrete windows of time rather than continuously. Such time sampling may be valuable for implantable systems or systems having implantable components as the power and processing requirements may be reduced relative to continuous monitoring.

It will be understood that the processes, and components thereof, described above with regard to FIGS. 1-7, as well as the illustrative examples presented in and described above with regard to FIG. 8, are provided for purposes of illustration and not limitation. Process steps other than those described herein, or derivations of the steps or components to carry out the steps, may be employed. Further, process steps depicted and discussed above may be interchanged, substituted, added to, or omitted from processes of alternative embodiments, as appropriate.

The processes described above may be employed with any suitable device or system for removing fluid, or fluid and contaminants, from blood. The devices, or components thereof, may be traditional large counsel-type, wearable, or implantable.

Figure 9:
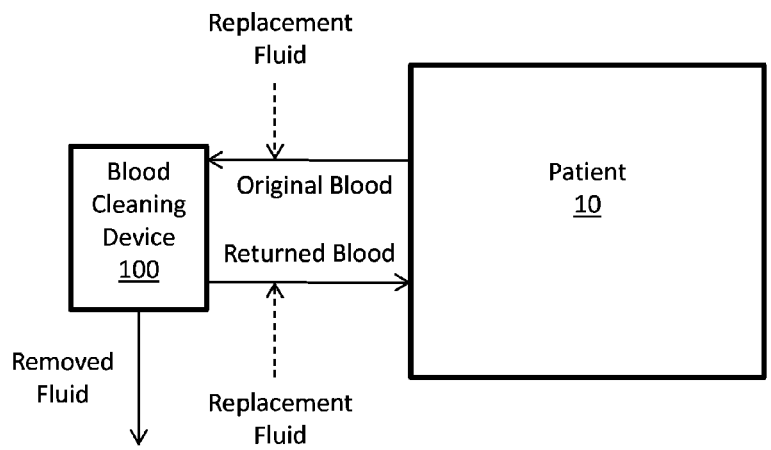
FIGS. 9-11 are schematic block diagrams showing interaction of blood fluid removal devices with a patient showing flow of blood (dashed arrows) and fluid (solid arrows), which blood fluid removal devices may be used in various embodiments described herein.
Figure 10:
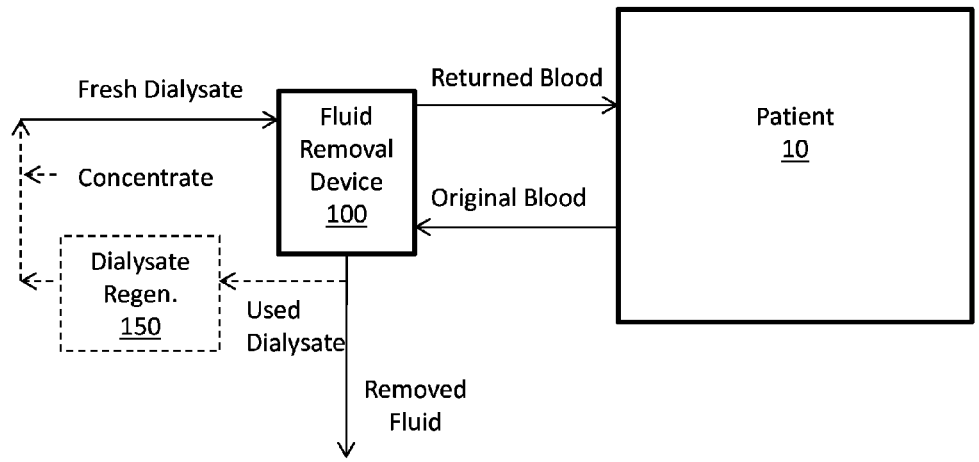
Figure 11:
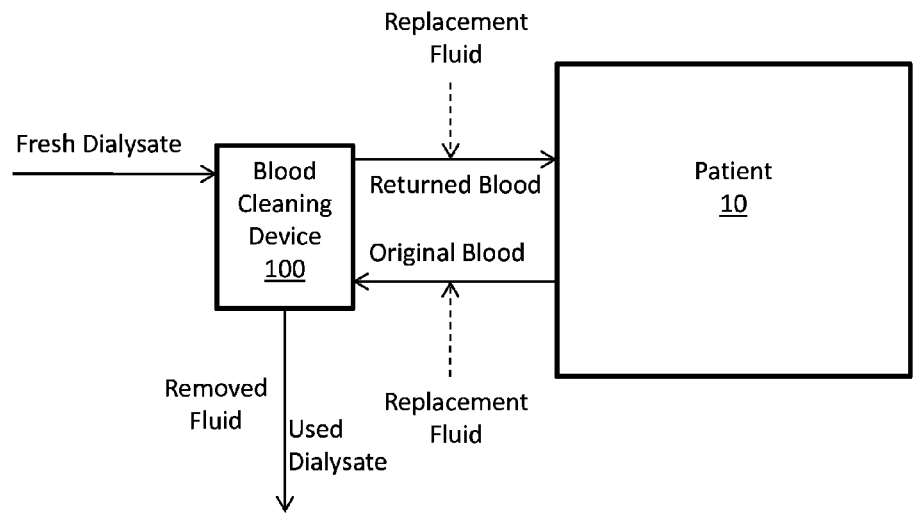

Block diagrams of some example devices and systems are shown in FIGS. 9-11. As shown in FIG. 9, blood may be removed from a patient 10 and fluid may be removed via a blood fluid removal device 100 and returned to the patient 10. Removed fluid may be diverted. In some embodiments where the blood fluid removal device 100 or system, or components thereof, are implanted, the removed fluid may be diverted to the patient's bladder. Examples of blood fluid removal devices 100 that may operate as depicted in FIG. 9 are ultrafiltration and hemofiltration devices. Examples of such devices and components thereof that may be employed in accordance with the teachings presented herein are well known in the art. With some of such devices, replacement fluid may be introduced into the patient's blood if fluid is removed from the blood by the device 100 at too great of a rate or amount. The replacement fluid may be added to the original blood before fluid removal or may be added to the blood after initial fluid removal and prior to return to the patient's cardiovascular system. Preferably, the replacement fluid is added after initial fluid removal. The pH and electrolyte concentration of the replacement fluid may be set or adjusted, e.g. as described in more detail below.

As shown in the embodiment depicted in FIG. 10, the blood fluid removal device 100 may employ dialysate to assist in removal of contaminants from the patient's blood and in maintaining proper pH and electrolyte balance. The pH or electrolyte concentration of the dialysate may be set or adjusted, e.g. as described in more detail below. Used dialysate and fluid removed from the blood may be diverted. In some embodiments, particularly where the blood fluid removal device 100 or system or components thereof are wearable or implantable, the used dialysate and removed fluid, or a portion thereof, may be regenerated (indicated by dashed lined regeneration system 150) to produce fresh dialysate for re-use in the blood fluid removal process. One system for regeneration of dialysate is the REDY system, such as described in Roberts, M, "The regenerative dialysis (REDY) sorbent system," *Nephrology* 4:275-278, 1998, which system may be employed or readily modified for use in embodiments described herein. As shown in FIG. 10, a concentrate may be added to the regenerated dialysate to adjust the pH and electrolytes of the regenerated dialysate to an amount suitable for re-use as fresh dialysate.

Regardless of whether the dialysate is regenerated, systems and devices that operate in a manner shown in the embodiment of FIG. 10 include hemodialysis and hemodiafiltration systems. Examples of such devices and components thereof that may be employed in accordance with the teachings presented herein are well known in the art. It will be understood that peritoneal dialysis, where the dialysate is introduced into peritoneal cavity may also be employed.

As shown in FIG. 11, in cases where the blood fluid removal device 100 of FIG. 10 removes fluid from the blood at too high of a rate, replacement fluid may be introduced into the patient's blood, upstream or downstream of fluid removal, e.g. as described above with regard to FIG. 9.

Regardless of the device or blood fluid removal process employed, system parameters such as rate of fluid removal, blood flow rate or electrolyte or pH buffer component or concentration may be controlled. Some schematic block diagrams for controlling electrolyte or pH of a dialysate or replacement fluid (and thus of blood) are shown in FIG. 12, in which representative components of an example of a closed-loop system for adjusting pH and electrolyte concentrations of fluid are shown.

Figure 12:
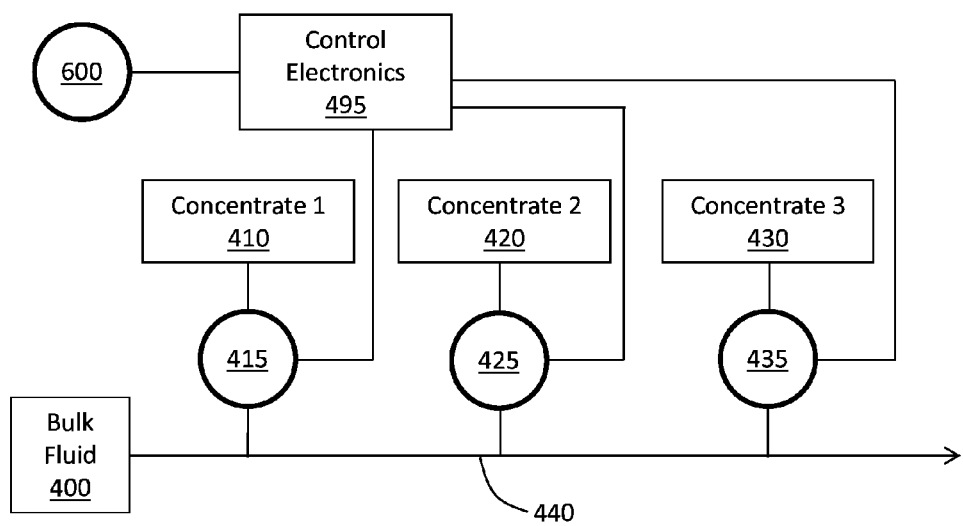
FIG. 12 is a schematic block diagram showing flow paths and some control mechanisms for controlling flow of concentrate into fluid for use in a blood fluid removal process.

With reference to FIG. 12, input data 600 (e.g. input 600 as discussed above with regard to FIG. 2) or "learned" parameters may be presented to, or processed within, control electronics 495, which are configured to control flow control elements 415, 425, 435, such as valves. The electronically controllable flow control elements 415, 425, 435 are in fluid communication with supplies of concentrated electrolyte or buffer solutions 410, 420, 430 and with fluid line 440, which may be a catheter for carrying fresh dialysate or a catheter for carrying replacement fluid. The electronically controllable flow control elements 415, 425, 435, via control electronics 495, control the rate at which the concentrates 410, 420, 430 flow into the fluid line 440. The concentrates 410, 420, 430 are added to bulk fluid 400 to adjust the concentration of electrolytes or the pH of the bulk fluid (and thus the blood).

Any number of suitable concentrates may be used. For example, one concentrate may be sufficient with higher amounts being added when the electrolytes are determined to be low in the patient's blood, and smaller amounts being added when the electrolytes are determined to be high in the patient's blood. More than one concentrate may be used when it is desired to, for example, control pH and electrolyte concentration independently or to control concentration of different electrolytes independently.

Control elements 415, 425, 435, as depicted in FIG. 12 and discussed above, may be any suitable control element, such as electronically controllable valves, electronically controllable pump mechanisms, or the like.

Any suitable system may be configured as depicted in FIG. 12 to provide control of adjustment of pH or electrolytes based on input data 600 or "learned" parameters. By way of example, selected components of two example systems are illustrated in FIGS. 13-14.

Figure 13:
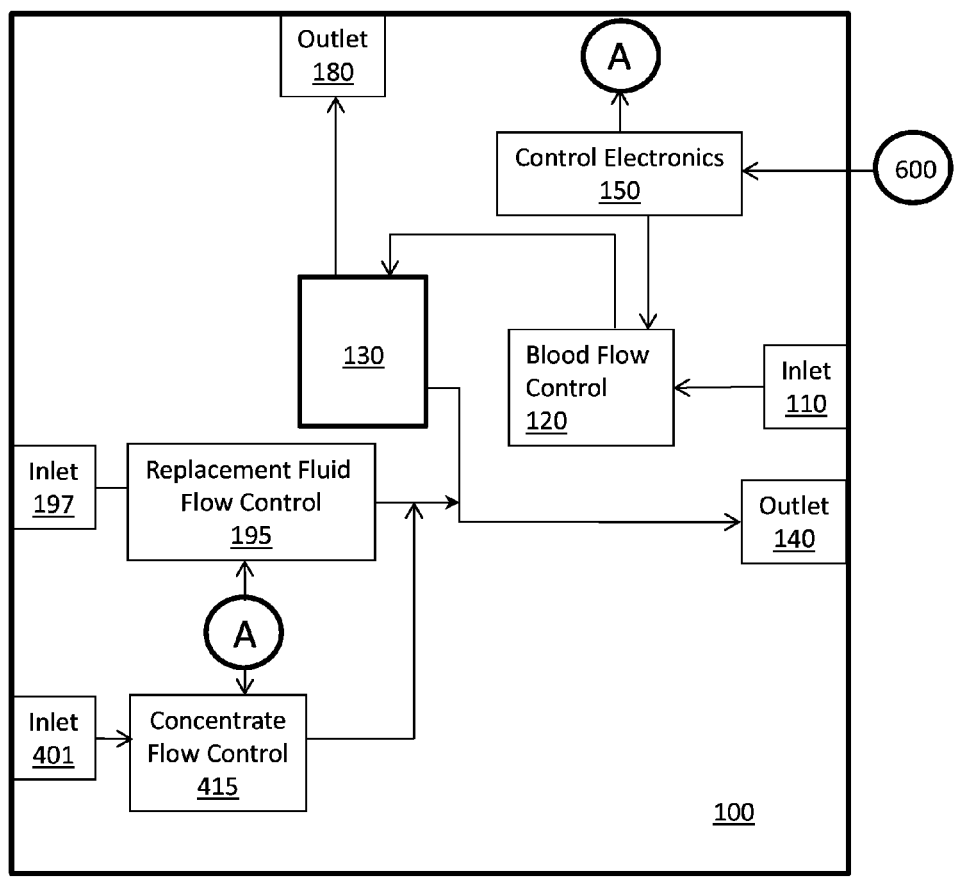
FIGS. 13-14 are schematic block diagrams of some components of blood fluid removal devices that are configured to various system parameters.
Figure 14:
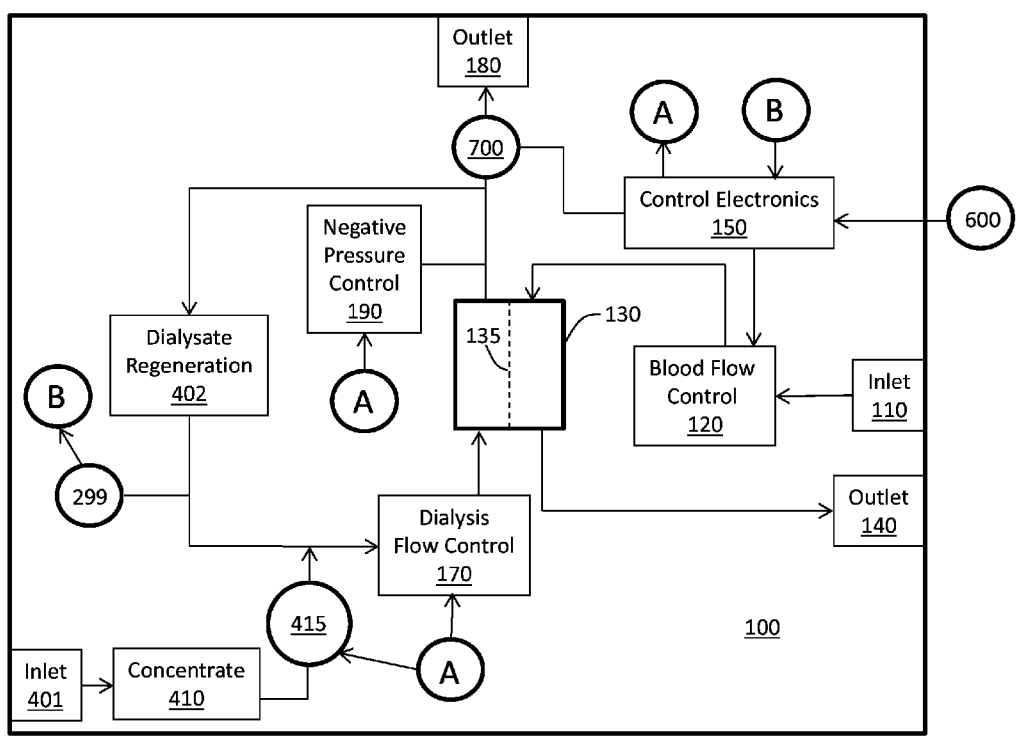

Referring now to FIG. 13, the depicted device 100 includes a fluid pathway for adding replacement fluid to blood before it is returned to the patient. The device 100 includes an inlet 110 for receiving blood from the patient and an outlet 140 for returning blood to the patient. In the flow path between the inlet 110 and outlet 140 are a blood flow control element 120 and a medium for removing fluid and contaminants from the blood. The blood flow control element 120 is operably coupled to control electronics 150 which provide instructions to control the rate at which blood is passed through medium 130. Fluids and contaminants removed from the blood by the medium 130 may exit via outlet 180.

The device 100 depicted in FIG. 13 also includes an inlet 197 for receiving bulk replacement fluid and a replacement fluid flow control element 195 in communication with the inlet and configured to control the rate at which the replacement fluid is added to the blood. The control electronics 150 are operably coupled to the replacement fluid flow control element 195 and are configured to control the rate at which replacement fluid flow control element 195 adds fluid to the blood. The device 100 also includes (i) an inlet 401 for receiving a concentrate for adjusting the pH or electrolyte concentration of the bulk replacement fluid, and (ii) a concentrate flow control element 415 in communication with the inlet 401 and configured to control the rate at which the concentrate is added to the replacement fluid or blood before the blood is returned to the patient. Preferably, the concentrate is added to the replacement fluid prior to the replacement fluid being added to the blood (as depicted) so that the concentrate may be mixed or diluted prior to being added to the blood. The device may include a mixer (not shown) to mix the concentrate and bulk replacement fluid prior to adding to the blood.

In the device depicted in FIG. 13, the control electronics 150 are operably coupled to the concentrate flow control element 415 and are configured to control the rate at which the concentrate flow control element 415 adds fluid to the replacement fluid or blood. By controlling the rate at which the concentrate is introduced into replacement fluid or blood, the concentration or pH (or buffering capacity) of the returned blood can be controlled.

Referring now to FIG. 14, in which components that are numbered the same as in FIG. 13 refer to the same or similar components, a schematic block diagram of selected components of a blood fluid removal device 100 is shown. In the embodiment depicted in FIG. 14, the device has in inlet 110 for receiving blood from a patient, a blood flow control element 120 in communication with the inlet 110 and configured to control the rate at which blood flows through medium 130 for removing fluid and contaminates from the blood. The device also includes an outlet 140 in communication with the medium 130 for returning blood to the patient. In the depicted embodiment, the medium 130 includes a semipermeable filter 135, such as a hemodialysis or hemodiafiltration filter. The membrane separates a blood flow compartment from a dialysis flow compartment of the medium component 130.

In the embodiment depicted in FIG. 14, used dialysate is regenerated by passing through dialysate regeneration medium 402 or components, such REDY regeneration medium and components, or the like, to regenerate bulk dialysate. The device also has an outlet 180 in communication with the medium 130 for diverting fluid removed from the blood out of the device. A flow regulator element 700, such as a valve, is operably coupled to control electronics 150 and is disposed in the flow path between the medium 130 and the outlet 180 to control the amount of fluid that exits the device (as a portion of the fluid is regenerated). Often, the regeneration media or components (402) remove much of the pH buffer or electrolytes from the dialysate. Accordingly, a concentrate containing concentrated electrolytes and pH buffers is added to the regenerated dialysate before the dialysate re-enters the medium 130. In some embodiments, a sensor 299 is positioned downstream of the regeneration medium 402 to monitor a level of a component of the regenerated dialysate. The sensor 299 may be a pH or electrolyte sensor and data acquired from sensor 299 may be used in determining how much concentrate to add to the regenerated fluid (which data may be provided to control electronics 150). The sensor 299 may be a sensor that monitors a blood waste product, such as urea, to determine whether the regeneration media 402 is properly functioning. Increased or detectable levels of a waste product may indicate that the regeneration media 402 or components may need replacement or regeneration.

In the depicted embodiment, the concentrate 410 is stored in a reservoir 410, having an inlet 401 that allows the concentrate supply in the reservoir 410 to be replenished from time to time. The rate at which the concentrate is added to the regenerated dialysate is controlled by concentrate flow control element 415, which is operably coupled to control electronics 150, and may be based on input data 600 or "learned" parameters as described above.

The device 100 in FIG. 14 also has a dialysis flow control element 170 for controlling the rate at which dialysis is introduced into the dialysis flow compartment of the medium 130.

In the depicted embodiment, the device 100 also includes a negative pressure control element 190 in communication with the dialysate compartment of the medium component 130. The negative pressure control element 190, which may include a vacuum pump or the like, may be used to generate or change a pressure differential across the membrane to control the rate at which fluid is removed from blood that passes though the medium component 130.

The control electronics 150, which may include a processor, memory, etc., are operably coupled to, and configured to control, the blood flow control element 120, the dialysis flow control element 170, and the negative pressure control element 190. By controlling these elements in a coordinated manner, the rate at which fluid is removed from blood may be controlled. It will be understood that a device 100 need not have all of the controllable elements (120, 170, 190) depicted in FIG. 14 to effectively control rate of fluid removal from blood.

Any suitable control element may be used for the various control elements (120, 150, 170, 195, 415) depicted in FIGS. 13-14. For example, a variable or adjustable rate pump may be employed. Alternatively or in addition, a series of electronically controllable valves may be employed. In some embodiments, the valves are in communication flow paths having differing flow resistances.

While FIGS. 13-14 depict components as being within a single unit, it will be understood that one or more of the components may be housed in separate units. For example, the control electronics, or a portion thereof, may be housed in a separate device, such as a computer, tablet, physician programmer, or the like. The computer, tablet, etc. may receive input from sensors, determine appropriate action to take, and instruct appropriate components of a blood fluid removal device to take the appropriate action.

It will be understood that the blood fluid removal devices and systems, and components thereof, described herein are presented for purposes of illustration and not limitation. Components, devices and systems other than those described herein, or derivations of the components, devices and systems described herein, may be employed. Further, components of the devices depicted and discussed above may be interchanged, substituted or added to components of alternative embodiments, as appropriate. Further, it will be understood that, while many of the blood fluid removal devices depicted in a variety of the figures, such as FIGS. 9-11, are shown as external to the patient, the teachings presented herein apply if the device, or components thereof, were implanted in the patient.

The devices and systems described above, or components thereof, may be used to carry out the methods depicted in FIGS. 1-7, or portions thereof. Of course, any suitable device or system may be employed to carry out the methods, or portions thereof, described above.

The methods described herein, including the methods depicted in FIGS. 1-7, may be carried out by blood fluid removal devices or systems, or other devices in communication with blood fluid removal devices or systems. These methods may be algorithms or instructions programmed into memory of such devices, which may be carried out by processors or other control electronics of the devices. Preferably, the processor is in communication with appropriate control elements of the devices and is configured to control such elements in a manner such that the programmed instructions are carried out by the appropriate device. It will be understood that a computer-readable medium programmed with instructions that cause a sensor device, blood fluid removal device, or other suitable device to carry out a method, or a portion thereof, as described herein are contemplated. The computer-readable medium may be non-transitory, i.e. lasting for more than a fleeting instant or seconds. The medium may be memory, such as RAM or ROM, a cd or dvd, flash memory, or the like.

Various aspects of methods, devices, systems, computer-readable media, and the like are described herein. A summary of some of selected aspects described herein is presented below.

In a $1^{st}$ aspect, a method carried out by a blood fluid removal system, comprises (i) initiating a blood fluid removal session with initial system parameters; (ii) acquiring a first set of data regarding one or more patient physiological parameters; (iii) storing the first data set in a "most effective to date" data set memory; (iv) associating the initial system parameters in an increased effectiveness lookup table with the first data set; (v) adjusting at least one parameter of the blood fluid removal session to arrive at adjusted system parameters; (vi) acquiring a second set of data regarding the one or more patient physiological parameters after the at least one parameter of the blood fluid removal session has been adjusted; and (vii) if at least one value of the second data set is closer to the target value than a corresponding at least one value of the first data set: replacing the first data set in the most effective to date data set memory with the second data set; storing in the increased effectiveness lookup table data regarding the second data set; and associating data regarding the adjusted system parameters with the second data set.

A $2^{nd}$ aspect is a method of the $1^{st}$ aspect, further comprising: (i) storing the first data set in a least effective to date data set memory; (ii) associating the initial system parameters in a becoming less effective lookup table with the first data set prior to adjusting the at least one parameter of the blood fluid removal session; and (iii) if the at least one value of the second data set is not closer to the target value than the corresponding at least one value of the first data set: replacing the first data set in the least effective to date data set memory with the second data set; storing in the becoming less effective lookup table data regarding the second data set; and associating data regarding the adjusted system parameters with the second data set.

A $3^{rd}$ aspect is a method of the $1^{st}$ or $2^{nd}$ aspect, further comprising: (i) further adjusting at least one parameter of the blood fluid removal session to arrive at further adjusted system parameters; (ii) acquiring a third set of data regarding the one or more patient physiological parameters after the at least one parameter of the blood fluid removal session has been further adjusted; and (iii) if at least one value of the third data set is closer to the target value than a corresponding at least one value stored in the most effective to date data set memory: replacing the data set in the most effective to date data set memory with the third data set; and storing in the increased effectiveness lookup table data regarding the third data set and associating data regarding the further adjusted system parameters with the third data set.

A $4^{th}$ aspect is a method of the $2^{nd}$ aspect, further comprising: (i) further adjusting at least one parameter of the blood fluid removal session to arrive at further adjusted system parameters; (ii) acquiring a fourth set of data regarding the one or more patient physiological parameters after the at least one parameter of the blood fluid removal session has been further adjusted; and (iii) if at least one value of the fourth data set is not closer to the target value than a corresponding at least one value stored in the least effective to date data set memory: replacing the data set in the least effective to date data set memory with the fourth data set; and storing in the becoming less effective lookup table data regarding the fourth data set and associating data regarding the further adjusted system parameters with the fourth data set.

A $5^{th}$ aspect is a method of any of aspects 1-4, further comprising: (i) acquiring a fifth set of data regarding one or more patient physiological parameters; (ii) comparing the fifth data set to the increased effectiveness lookup table; and (iii) adjusting the system parameters the system parameters associated with the data set stored in the increased effectiveness lookup table if at least one parameter of the data set stored in the improvement lookup table is within a predetermined range of at least one corresponding parameter of the fifth data set.

A $6^{th}$ aspect is a method of any of aspects 1-5, further comprising: (i) stopping the blood fluid removal session; (ii) acquiring a sixth set of data regarding one or more patient physiological parameters; (iii) comparing the sixth data set to the increased effectiveness lookup table; and (iv) initiating a second blood fluid removal session with the system parameters associated with the data set stored in the increased effectiveness lookup table if at least one parameter of the data set stored in the increased effectiveness lookup table is within a predetermined range of at least one corresponding parameter of the sixth data set.

A $7^{th}$ aspect is a method of any of aspects 1-6, wherein the at least one of the one or more patient parameters are selected from the group consisting of blood pressure, heart rate, pH and concentration of an electrolyte.

An $8^{th}$ aspect is method of the $7^{th}$ aspect, wherein the electrolyte is potassium.

A $9^{th}$ aspect is a method of any of aspects 1-8, wherein the system parameters comprise one or more of fluid removal rate and concentration of one or more electrolyte.

A $10^{th}$ aspect is a blood fluid removal system, comprising: (a) a blood fluid removal medium configured to remove blood from a patient, wherein blood enters the medium, fluid is removed from the blood, and blood exits the medium; (b) one or more control elements configured to control (i) the rate at which the medium removed fluid from the blood or (ii) the concentration of electrolytes or pH in the blood that exits the medium; (c) one or more sensors configured monitor one or more physiological parameter of the patient; and (d) control electronics comprising memory and a processor, wherein the control electronics are in operable communication with the one or more sensors and are operably coupled to the one or more control elements, wherein the control electronics are configured to carry out a method according to any of aspects 1-9.

An $11^{th}$ aspect is a system of the $10^{th}$ aspect, wherein the blood fluid removal medium and the control electronics are housed within a blood fluid removal device.

A 12th aspect is a system of the 10th or 11th aspect, further comprising a computer-readable medium, wherein the computer-readable medium comprises instructions that cause the control electronics to carry out the method according to any of aspects 1-9.

A $13^{th}$ aspect is a blood fluid removal system comprising: (a) a blood fluid removal medium configured to remove blood from a patient, wherein blood enters the medium, fluid is removed from the blood, and blood exits the medium; (b) one or more control elements configured to control (i) the rate at which the medium removed fluid from the blood or (ii) the concentration of electrolytes or pH in the blood that exits the medium; (c) one or more sensors configured monitor one or more physiological parameter of the patient; and (d) control electronics comprising memory and a processor, wherein the control electronics are in operable communication with the one or more sensors and are operably coupled to the one or more control elements, wherein the control electronics are configured to (i) initiate a blood fluid removal session with initial system parameters; (ii) acquire a first set of data regarding one or more patient physiological parameters; (iii) store the first data set in a most effective to date data set memory; (iv) associate the initial system parameters in an increased effectiveness lookup table with the first data set; (v) adjust at least one parameter of the blood fluid removal session to arrive at adjusted system parameters; (vi) acquire a second set of data regarding the one or more patient physiological parameters after the at least one parameter of the blood fluid removal session has been adjusted; and (vii) if at least one value of the second data set is closer to a target value than a corresponding at least one value of the first data set: replace the first data set in the most effective to date data set memory with the second data set; store in the increased effectiveness lookup table data regarding the second data set; and associate data regarding the adjusted system parameters with the second data set.

A $14^{th}$ aspect is a computer-readable medium comprising instructions that, when executed by a blood fluid removal device, cause the device to (i) initiate a blood fluid removal session with initial system parameters; (ii) acquire a first set of data regarding one or more patient physiological parameters; store the first data set in a most effective to date data set memory; (iii) associate the initial system parameters in an increased effectiveness lookup table with the first data set; (iv) adjust at least one parameter of the blood fluid removal session to arrive at adjusted system parameters; (v) acquire a second set of data regarding the one or more patient physiological parameters after the at least one parameter of the blood fluid removal session has been adjusted; and (vi) if at least one value of the second data set is closer to a target value than a corresponding at least one value of the first data set: replace the first data set in the most effective to date data set memory with the second data set; store in the increased effectiveness lookup table data regarding the second data set; and associate data regarding the adjusted system parameters with the second data set.

A $15^{th}$ aspect is a method carried out by a blood fluid removal system, comprising: (a) acquiring data regarding one or more of: (i) one or more patient physiological parameters; and (ii) time since last blood fluid removal session; (b) acquiring data regarding one or more target outcomes of a blood fluid removal session; (c) comparing the data regarding at least one of the one or more target outcomes of the blood fluid session to corresponding data regarding at least one prior patient outcome stored in a lookup table, wherein the lookup table comprises data regarding system parameters used in one or more prior blood fluid removal sessions of the patient and comprises patient data prior to the previous session regarding one or more of (i) one or more patient physiological parameters; and (ii) time since last blood fluid removal session; (d) comparing the data regarding the one or more of (i) one or more patient physiological parameters; and (ii) time since last blood fluid removal session to corresponding patient data prior to the previous session stored in the lookup table; and (e) initiating a blood fluid removal session employing the system parameters used the prior blood fluid removal session if the at least one of the one or more target outcomes is within a predetermined range of the corresponding data regarding the at least one prior patient outcome stored in the lookup table and the data regarding the one or more of (i) one or more patient physiological parameters; and (ii) time since last blood fluid removal session is within a predetermined range of the corresponding patient data prior to the previous session stored in the lookup table.

A $16^{th}$ aspect is a method of the 15th aspect, wherein the at least one of the one or more patient parameters are selected from the group consisting of blood pressure, heart rate, pH and concentration of an electrolyte.

A $17^{th}$ aspect is method of the $16^{th}$ aspect, wherein the electrolyte is potassium.

An $18^{th}$ aspect is a method of any of aspects 15-17, wherein the system parameters comprise one or more of fluid removal rate and concentration of one or more electrolyte.

A $19^{th}$ aspect is a blood fluid removal system, comprising: (a) a blood fluid removal medium configured to remove blood from a patient, wherein blood enters the medium, fluid is removed from the blood, and blood exits the medium; (b) one or more control elements configured to control (i) the rate at which the medium removed fluid from the blood or (ii) the concentration of electrolytes or pH in the blood that exits the medium; (c) one or more sensors configured monitor one or more physiological parameter of the patient; (d) an input configured to allow entry of data regarding patient or system parameters; and (e) control electronics comprising memory and a processor, wherein the control electronics are in operable communication with the one or more sensors and are operably coupled to the one or more control elements and the input, wherein the control electronics are configured to carry out a method according to any of aspects 15-18.

A $20^{th}$ aspect is a system of the $19^{th}$ aspect, wherein the blood fluid removal medium and the control electronics are housed within a blood fluid removal device.

A 21st aspect is a system of the 19th or 20th aspect, further comprising a computer-readable medium, wherein the computer-readable medium comprises instructions that cause the control electronics to carry out the method according to any of aspects 15-18.

A $22^{nd}$ aspect is a blood fluid removal system comprising: (a) a blood fluid removal medium configured to remove blood from a patient, wherein blood enters the medium, fluid is removed from the blood, and blood exits the medium; (b) one or more control elements configured to control (i) the rate at which the medium removed fluid from the blood or (ii) the concentration of electrolytes or pH in the blood that exits the medium; (c) one or more sensors configured monitor one or more physiological parameter of the patient; (d) an input configured to allow entry of data regarding patient or system parameters; and (e) control electronics comprising memory and a processor, wherein the control electronics are in operable communication with the one or more sensors and are operably coupled to the one or more control elements and the input, wherein the control electronics are configured to: (i) acquire data regarding one or more of: one or more patient physiological parameters; and time since last blood fluid removal session; (ii) acquire data regarding one or more target outcomes of a blood fluid removal session; (iii) compare the data regarding at least one of the one or more target outcomes to corresponding data regarding at least one prior patient outcome stored in a lookup table, wherein the lookup table comprises data regarding system parameters used in one or more prior blood fluid removal sessions of the patient and comprises patient data prior to the previous session regarding one or more of (i) one or more patient physiological parameters; and (ii) time since last blood fluid removal session; (iv) compare the data regarding the one or more of (i) one or more patient physiological parameters; and (ii) time since last blood fluid removal session to corresponding patient data prior to the previous session stored in the lookup table; and (v) initiate a blood fluid removal session employing the system parameters used in the prior blood fluid removal session if the at least one of the one or more target outcomes is within a predetermined range of the corresponding data regarding the at least one prior patient outcome stored in the lookup table and the data regarding the one or more of (i) one or more patient physiological parameters; and (ii) time since last blood fluid removal session is within a predetermined range of the corresponding patient data prior to the previous session stored in the lookup table.

A $23^{rd}$ aspect is a computer-readable medium comprising instructions that, when executed by a blood fluid removal device, cause the device to (i) acquire data regarding one or more of: one or more patient physiological parameters; and time since last blood fluid removal session; (ii) acquire data regarding one or more target outcomes of a blood fluid removal session; (iii) compare the data regarding the at least one of the one or more target outcomes to corresponding data regarding at least one prior patient outcome stored in a lookup table, wherein the lookup table comprises data regarding system parameters used in one or more prior blood fluid removal sessions of the patient and comprises patient data prior to the previous session regarding one or more of one or more patient physiological parameters and time since last blood fluid removal session; (iv) compare the data regarding the one or more of (i) one or more patient physiological parameters; and (ii) time since last blood fluid removal session to corresponding patient data prior to the previous session stored in the lookup table; and (v) initiate a blood fluid removal session employing the system parameters used in the prior blood fluid removal session if the at least one of the one or more target outcomes is within a predetermined range of the corresponding data regarding the at least one prior patient outcome stored in the lookup table and the data regarding the one or more of (i) one or more patient physiological parameters; and (ii) time since last blood fluid removal session is within a predetermined range of the corresponding patient data prior to the previous session stored in the lookup table.

A $24^{th}$ aspect is a method carried out by a blood fluid removal system, comprising: (i) collecting first data regarding a patient, the data including one or more of a physiological parameter and time since last blood fluid removal session; (ii) collecting second data regarding system parameters employed in blood fluid removal sessions of the patient; (iii) determining, based on the first and second collected data, whether at least one physiological parameter of the patient became more effective as a result of the system parameters employed; (iv) determining whether a value of current patient data is within a predetermined range of a corresponding value of first collected data; and (v) employing the system parameters that resulted in increased effectiveness, if such parameters are determined to exist and if the current patient data is determined to be within the predetermined range.

A $25^{th}$ aspect is a blood fluid removal system, comprising: (a) a blood fluid removal medium configured to remove blood from a patient, wherein blood enters the medium, fluid is removed from the blood, and blood exits the medium; (b) one or more control elements configured to control (i) the rate at which the medium removed fluid from the blood or (ii) the concentration of electrolytes or pH in the blood that exits the medium; (c) one or more sensors configured monitor one or more physiological parameter of the patient; (d) an input configured to allow entry of data regarding patient or system parameters; and (e) control electronics comprising memory and a processor, wherein the control electronics are in operable communication with the one or more sensors and are operably coupled to the one or more control elements and the input, wherein the control electronics are configured to carry out a method according to aspect 24.

A $26^{th}$ aspect is a system of the $25^{th}$ aspect, wherein the blood fluid removal medium and the control electronics are housed within a blood fluid removal device.

A 27th aspect is a system of the 25th or 26th aspect, further comprising a computer-readable medium, wherein the computer-readable medium comprises instructions that cause the control electronics to carry out the method according to the 24th aspect.

A $28^{th}$ aspect is a blood fluid removal system comprising: (a) a blood fluid removal medium configured to remove blood from a patient, wherein blood enters the medium, fluid is removed from the blood, and blood exits the medium; (b) one or more control elements configured to control (i) the rate at which the medium removed fluid from the blood or (ii) the concentration of electrolytes or pH in the blood that exits the medium; (c) one or more sensors configured monitor one or more physiological parameter of the patient; (d) an input configured to allow entry of data regarding patient or system parameters; and (e) control electronics comprising memory and a processor, wherein the control electronics are in operable communication with the one or more sensors and are operably coupled to the one or more control elements and the input, wherein the control electronics are configured to: (i) collect first data regarding a patient, the data including one or more of a physiological parameter and time since last blood fluid removal session; (ii) collect second data regarding system parameters employed in blood fluid removal sessions of the patient; (iii) determine, based on the first and second collected data, whether at least one physiological parameter of the patient became more effective as a result of the system parameters employed; (iv) determine whether a value of current patient data is within a predetermined range of a corresponding value of first collected data; and (v) employ the system parameters that resulted in increased effectiveness, if such parameters are determined to exist and if the current patient data is determined to be within the predetermined range.

A $29^{th}$ aspect is a computer-readable medium comprising instructions that, when executed by a blood fluid removal device, cause the device to (i) collect first data regarding a patient, the data including one or more of a physiological parameter and time since last blood fluid removal session; (ii) collect second data regarding system parameters employed in blood fluid removal sessions of the patient; (iii) determine, based on the first and second collected data, whether at least one physiological parameter of the patient became more effective as a result of the system parameters employed; (iv) determine whether a value of current patient data is within a predetermined range of a corresponding value of first collected data; and (v) employ the system parameters that resulted in increased effectiveness, if such parameters are determined to exist and if the current patient data is determined to be within the predetermined range.

A 30th aspect is a method comprising: (i) storing system parameters from a first blood fluid removal session in memory; (ii) acquiring a first set of data regarding one or more patient parameters following the first session but before a second session; (iii) storing the first data set in a most effective to date data set memory; (iv) associating the first system parameters in an increased effectiveness lookup table with the first data set; (v) storing system parameters from the second blood fluid removal session in memory; (vi) acquiring a second set of data regarding the one or more patient parameters following the second session; (vii) determining whether at least one value of the second data set is closer to a target value than at least one corresponding value of the first data set; and (viii) if the at least one value of the second data set is determined to be closer to the target value than the corresponding at least one value of the first data set: replacing the first data set in the most effective to date data set memory with the second data set; storing in the increased effectiveness lookup table data regarding the second data set; and associating data regarding the second system parameters with the second data set.

A 31$^{st}$ aspect is a method of the 30$^{th}$ aspect, further comprising: (i) storing the first data set in a least effective to date data set memory; (ii) associating the first system parameters in a decreased effectiveness lookup table with the first data set; and (iii) if the at least one value of the second data set is determined not to be closer to the target value than the corresponding at least one value of the first data set: replacing the first data set in the least effective to date data set memory with the second data set; storing in the decreased effectiveness lookup table data regarding the second data set; and associating data regarding the second system parameters with the second data set.

A 32$^{nd}$ aspect is a method of the 30$^{th}$ or 31$^{st}$ aspect, further comprising: (i) storing system parameters for a third blood fluid removal session in memory; (ii) acquiring a third set of data regarding the one or more patient parameters following the third session; (iii) determining whether at least one value of the third data set is closer to a target value than at least one corresponding value stored in the most effective to date data set memory; and (iv) if the at least one value of the third data set is determined to be closer to the target value than the corresponding at least one value stored in the most effective to date data set memory: replacing the data set in the most effective to date data set memory with the third data set; and storing in the increased effectiveness lookup table data regarding the third data set and associating data regarding the third system parameters with the third data set.

A 33$^{rd}$ aspect is a method of the 30$^{th}$ or 31$^{st}$ aspect, further comprising: (i) storing system parameters from a fourth blood fluid removal session in memory; (ii) acquiring a fourth set of data regarding the one or more patient parameters following the fourth session; (iii) determining whether at least one value of the fourth data set is further from a target value than at least one corresponding value stored in the least effective to date data set memory; and (iv) if the at least one value of the fourth data set is determined not to be closer to the target value than the corresponding at least one value stored in the least effective to date data set memory: replacing the data set in the least effective to date data set memory with the fourth data set; and storing in the decreased effectiveness lookup table data regarding the fourth data set and associating data regarding the fourth system parameters with the fourth data set.

A 34$^{th}$ aspect is a method of any of aspects 30-33, further comprising: (i) acquiring a fifth set of data regarding one or more patient parameters; (ii) consulting the increased effectiveness lookup table to determine whether at least one parameter of a data set stored in the increased effectiveness lookup table is within a predetermined range of the fifth data set; and (iii) setting system parameters for a next blood fluid removal session to the system parameters associated with the data set stored in the increased effectiveness lookup table.

A 35$^{th}$ aspect is a method of any of aspects 30-35, wherein the at least one of the one or more patient parameters are selected from the group consisting of blood pressure, heart rate, pH and concentration of an electrolyte.

A 36$^{th}$ aspect is a method of the 35$^{th}$ aspect, wherein the electrolyte is potassium.

A 37$^{th}$ aspect is a method of any of aspects 30-36, wherein the system parameters comprise one or more of fluid removal rate and concentration of one or more electrolyte.

A 38$^{th}$ aspect is a method of any of aspects 30-37, wherein the method is carried out by a blood fluid removal system.

A 39$^{th}$ aspect is a blood fluid removal system, comprising: (a) a blood fluid removal medium configured to remove blood from a patient, wherein blood enters the medium, fluid is removed from the blood, and blood exits the medium; (b) one or more control elements configured to control (i) the rate at which the medium removed fluid from the blood or (ii) the concentration of electrolytes or pH in the blood that exits the medium; (c) one or more sensors configured monitor one or more physiological parameter of the patient; and (d) control electronics comprising memory and a processor, wherein the control electronics are in operable communication with the one or more sensors and are operably coupled to the one or more control elements, wherein the control electronics are configured to carry out a method according to any of aspects 30-38.

A 40$^{th}$ aspect is a system of the 39$^{th}$ aspect, wherein the blood fluid removal medium and the control electronics are housed within a blood fluid removal device.

A 41st aspect is a system of the 39th or 40th aspects, further comprising a computer-readable medium, wherein the computer-readable medium comprises instructions that cause the control electronics to carry out the method according to any of aspects 30-38.

A 42$^{nd}$ aspect is a blood fluid removal system comprising: (a) a blood fluid removal medium configured to remove blood from a patient, wherein blood enters the medium, fluid is removed from the blood, and blood exits the medium; (b) one or more control elements configured to control (i) the rate at which the medium removed fluid from the blood or (ii) the concentration of electrolytes or pH in the blood that exits the medium; (c) one or more sensors configured monitor one or more physiological parameter of the patient; and (d) control electronics comprising memory and a processor, wherein the control electronics are in operable communication with the one or more sensors and are operably coupled to the one or more control elements, wherein the control electronics are configured to (i) store system parameters from a first blood fluid removal session in memory; (ii) acquire a first set of data regarding one or more patient parameters following the first session but before a second session; (iii) store the first data set in a most effective to date data set memory; (iv) associate the first system parameters in an increased effectiveness lookup table with the first data set; (v) store system parameters from the second blood fluid removal session in memory; (vi) acquire a second set of data regarding the one or more patient parameters following the second session; (vii) determine whether at least one value of the second data set is closer to a target value than at least one corresponding value of the first data set; and (viii) if the at least one value of the second data set is determined to be closer to the target value than the corresponding at least one value of the first data set: replace the first data set in the most effective to date data set memory with the second data set; store in the increased effectiveness lookup table data regarding the second data set; and associate data regarding the second system parameters with the second data set.

A $43^{rd}$ aspect is a computer-readable medium comprising instructions that, when executed by a blood fluid removal device, cause the device to (i) store system parameters from a first blood fluid removal session in memory; (ii) acquire a first set of data regarding one or more patient parameters following the first session but before a second session; (iii) store the first data set in a most effective to date data set memory; (iv) associate the first system parameters in an increased effectiveness lookup table with the first data set; (v) store system parameters from the second blood fluid removal session in memory; (vi) acquire a second set of data regarding the one or more patient parameters following the second session; (vii) determine whether at least one value of the second data set is closer to a target value than at least one corresponding value of the first data set; and (viii) if the at least one value of the second data set is determined to be closer to the target value than the corresponding at least one value of the first data set: replace the first data set in the most effective to date data set memory with the second data set; store in the increased effectiveness lookup table data regarding the second data set; and associate data regarding the second system parameters with the second data set.

Thus, systems, devices and methods for INTERSESSION MONITORING FOR BLOOD FLUID REMOVAL THERAPY are described. Those skilled in the art will recognize that the preferred embodiments described herein may be altered or amended without departing from the true spirit and scope of the disclosure, as defined in the accompanying claims.

In the claims that follow and the preceding aspects, the designators "first", "second", "third" and the like are used for purposes of distinguishing between elements and not for purposes of enumerating the elements or for defining a sequence of the elements. For example, a "third" data set does not necessarily imply that there are three data sets but rather that the "third" data set is distinct from the "first" data set. By way of further example, a "third" data set need not be obtained after a "first" data set.

What is claimed is:

1. A method of using a blood fluid removal system for tracking one or more physiological parameters of a patient, wherein the blood fluid removal system comprises:
    (a) a blood fluid removal medium configured to remove blood from the patient, wherein the blood enters the medium, a fluid contained in the blood is removed from the blood, and the blood exits the medium;
    (b) one or more control elements configured to control (i) a rate at which the medium removes fluid from the blood or (ii) concentration of electrolytes or pH in the blood that exits the medium;
    (c) one or more sensors configured to monitor the one or more physiological parameters of the patient wherein the physiological parameters are one or more selected from the group consisting of blood pressure, heart rate, pH and electrolyte concentration, the one or more sensors sensing signals from one or more of the blood and a tissue of the patient; and
    (d) control electronics comprising memory and a processor, wherein the control electronics are in operable communication with the one or more sensors and are operably coupled to the one or more control elements, wherein the control electronics are programmed to carry out the method of or for tracking the one or more physiological parameters of the patient, comprising:
    storing system parameters from a first blood fluid removal session in memory;
    acquiring a first set of data regarding the one or more physiological parameters of the patient following the first session but before a second blood fluid removal session;
    storing the first data set in a most effective to date data set in memory;
    associating the first system parameters in an increased effectiveness lookup table with the first data set;
    storing system parameters from the second blood fluid removal session in memory;
    acquiring a second set of data regarding the one or more physiological parameters of the patient following the second blood fluid removal session; and
    if at least one value of the second data set from the second blood fluid removal session is closer to a target value than a corresponding at least one value of the first data set from the first blood fluid removal session: replacing the first data set in the most effective to date data set in memory with the second data set; storing in the increased effectiveness lookup table data regarding the second data set; and
    associating data regarding the second system parameters with the second data set.

2. The method of claim 1, further comprising:
    storing the first data set in a least effective to date data set in memory;
    associating the first system parameters in a decreased effectiveness lookup table with the first data set;
    if the at least one value of the second data set from the second blood fluid removal session is not closer to the target value than the corresponding at least one value of the first data set from the first blood fluid removal session: replacing the first data set in the least effective to date data set memory with the second data set; storing in the decreased effectiveness lookup table data regarding the second data set; and associating data regarding the second system parameters with the second data set.

3. The method of claim 1, further comprising:
    storing system parameters for a third blood fluid removal session in memory; acquiring a third set of data regarding the one or more physiological parameters of the patient following the third session; and
    if at least one value of the third data set from the third blood fluid removal session is closer to the target value than a corresponding at least one value stored in the most effective to date data set memory: replacing the data set in the most effective to date data set memory with the third data set; and storing in the increased effectiveness lookup table data regarding the third data set, and associating data regarding the third system parameters with the third data set.

4. The method of claim 1, further comprising:
    storing system parameters from a fourth blood fluid removal session in memory; acquiring a fourth set of data regarding the one or more physiological parameters of the patient following the fourth session; and
    if at least one value of the fourth data set from the fourth blood fluid removal session is not closer to the target value than a corresponding at least one value stored in the least effective to date data set memory: replacing the data set in the least effective to date data set memory with the fourth data set; and storing in the decreased effectiveness lookup table data regarding the fourth data set, and associating data regarding the fourth system parameters with the fourth data set.

5. The method of claim 1, further comprising:
acquiring a fifth set of data regarding one or more physiological parameters of the patient; comparing the fifth data set to the increased effectiveness lookup table; and
setting system parameters for a next blood fluid removal session to system parameters associated with the data set stored in the increased effectiveness lookup table if at least one parameter of a data set stored in the increased effectiveness lookup table is within a predetermined range of the fifth data set.

6. The method of claim 1, wherein the at least one of the one or more physiological parameters of the patient are selected from the group consisting of blood pressure, heart rate, pH and concentration of an electrolyte.

7. The method of claim 6, wherein the electrolyte is potassium.

8. The method of claim 1, wherein the system parameters comprise one or more of fluid removal rate and concentration of one or more electrolyte.

9. A blood fluid removal system, comprising:
a blood fluid removal medium configured to remove blood from a patient, wherein the blood enters the medium,
a fluid contained in the blood is removed from the blood, and the blood exits the medium;
one or more control elements configured to control (i) a rate at which the medium removes fluid from the blood or (ii) concentration of electrolytes or pH in the blood that exits the medium;
one or more sensors configured to monitor one or more physiological parameters of the patient wherein the physiological parameters are one or more selected from the group consisting of blood pressure, heart rate, pH and electrolyte concentration, the one or more sensors sensing signals from one or more of the blood and a tissue of the patient; and
control electronics comprising memory and a processor, wherein the control electronics are in operable communication with the one or more sensors and are operably coupled to the one or more control elements, wherein the control electronics are programmed to carry out a first method of tracking the one or more physiological parameters of the patient comprising steps of:
storing system parameters from a first blood fluid removal session in memory;
acquiring a first set of data regarding the one or more physiological parameters of the patient following the first session but before a second blood fluid removal session; storing the first data set in a most effective to date data set in memory;
associating the first system parameters in an increased effectiveness lookup table with the first data set; storing system parameters from the second blood fluid removal session in memory; acquiring a second set of data regarding the one or more physiological parameters of the patient following the second blood fluid removal session; and
if at least one value of the second data set from the second blood fluid removal session is closer to a target value than a corresponding at least one value of the first data set from the first blood fluid removal session, replacing the first data set in the most effective to date data set in memory with the second data set, storing in the increased effectiveness lookup table data regarding the second data set, and associating data regarding the second system parameters with the second data set.

10. The system of claim 9, wherein the blood fluid removal medium and the control electronics are housed within a blood fluid removal device of the blood fluid removal system.

11. The system of claim 9, further comprising a computer-readable medium, wherein the computer-readable medium comprises instructions that cause the control electronics to carry out the first method.

12. A blood fluid removal system comprising:
a blood fluid removal medium configured to remove blood from a patient, wherein the blood enters the medium, a fluid contained in the blood is removed from the blood, and the blood exits the medium;
one or more control elements configured to control (i) a rate at which the medium removes fluid from the blood or (ii) concentration of electrolytes or pH in the blood that exits the medium;
one or more sensors configured to monitor one or more physiological parameters of the patient, wherein the one or more sensors sense signals from one or more of the blood or a tissue of the patient; and
control electronics comprising memory and a processor, wherein the control electronics are in operable communication with the one or more sensors and are operably coupled to the one or more control elements, wherein the control electronics are programmed to track the one or more physiological parameters of the patient to (i) store system parameters from a first blood fluid removal session in the memory; (ii) acquire a first set of data regarding the one or more physiological parameters of the patient following the first blood fluid removal session but before a second blood fluid removal session; (iii) store the first data set in a most effective to date data set in memory; (iv) associate the first system parameters in an increased effectiveness lookup table with the first data set; (v) store system parameters from the second blood fluid removal session in memory; (vi) acquire a second set of data regarding the one or more physiological parameters of the patient following the second blood fluid removal session; and (vii) if at least one value of the second data set from the second blood fluid removal session is closer to a target value than a corresponding at least one value of the first data set from the first blood fluid removal session, replace the first data set in the most effective to date data set in memory with the second data set, store in the increased effectiveness lookup table data regarding the second data set, and associate data regarding the second system parameters with the second data set.

13. The system of claim 9, wherein the first method further comprises the steps of:
storing the first data set in a least effective to date data set in memory;
associating the first system parameters in a decreased effectiveness lookup table with the first data set; and
if the at least one value of the second data set from the second blood fluid removal session is not closer to the target value than the corresponding at least one value of the first data set from the first blood fluid removal session: replacing the first data set in the least effective to date data set in memory with the second data set; storing in the decreased effectiveness lookup table data regarding the second data set; and associating data regarding the second system parameters with the second data set.

\* \* \* \* \*